(12) United States Patent
Duff et al.

(10) Patent No.: US 6,437,216 B1
(45) Date of Patent: Aug. 20, 2002

(54) TRANSGENIC MODELS OF INFLAMMATORY DISEASE

(75) Inventors: Gordon W. Duff; Martin Nicklin, both of Sheffield (GB)

(73) Assignee: Interleukin Genetics Inc., Waltham, MA (US)

( * ) Notice: Subject to any disclaimer, the term of this patent is extended or adjusted under 35 U.S.C. 154(b) by 0 days.

(21) Appl. No.: 09/647,826

(22) PCT Filed: Nov. 13, 1998

(86) PCT No.: PCT/US98/24287

§ 371 (c)(1),
(2), (4) Date: Mar. 12, 2001

(87) PCT Pub. No.: WO99/25857

PCT Pub. Date: May 27, 1999

(30) Foreign Application Priority Data

Nov. 13, 1997 (GB) .............................................. 9723835

(51) Int. Cl.⁷ .............................................. C12N 15/00
(52) U.S. Cl. ................................ 800/21; 800/18; 800/3; 435/320.1; 435/325; 536/23.1
(58) Field of Search ........................... 800/3, 8, 21, 18; 435/320.1, 325; 536/23.1

(56) References Cited

U.S. PATENT DOCUMENTS 5,487,992 A * 1/1996 Capecchi et al. ......... 435/172.3

FOREIGN PATENT DOCUMENTS

| WO | WO 96/09323 | 3/1996 |
| WO | WO 96/12792 | 5/1996 |
| WO | WO 98/40517 | 9/1998 |
| WO | WO 99/25857 | 5/1999 |

OTHER PUBLICATIONS

Sigmund; Viewpoint: Are Studies in Genetically Altered Mice Out of Control? 2000, Arterioscler Thromb Vasc Biol 20: 1425–1429.*

Kappel et. al.; Regulatiing gene expression in transgenic animals, 1992, Current Opinion in Biotechnology 3: 548–553.*

Mullins et. al.; Perpectives Series: Molecular Medicine in Genetically Engineered Animals, 1996 J. Clin. Invest. vol. 98, No. 11, S37–S40.*

Bradley et al.; Modifying The Mouse: Design and Desire, 1992, Biotechnology vol. 10: 534–539.*

Moreadith et. al.; Gene targeting in embryonic stem cells: the new physiology and metabolism, 1997, J. Mol. Med. 75: 208–216.*

Capecchi; Targeted Gene Replacement, 1994, Scientific American, 34–41.*

Zahedi et al.; The Mouse Interleukin 1 Receptor Antagonist Protein: Gene Structure and Regulation in Vitro, 1994, Cytokine vol. 6, No. 1: 1–9.*

Melton; Gene Targeting in the Mouse, 1994, BioEssays vol. 16, No. 9: 633–638.*

Hirsch et al.; "Functions of Interleukin 1 Receptor Antagonist in Gene Knochout and Overproducing Mice", Proc. Natl. Acad. Sc. USA, 93:11008–11013, (Oct. 1996).

Richardson et al.; "Interleukin 1 Gene Polymorphism Are Associated with Sigh–threatening Diabetic Retinopathy", Investigative Ophthalmology & Visual Science, 38(4) (Part 2): pp. 3714–3714 (Mar. 15, 1997).

International Search Report Completed on May 4, 1999 and mailed on May 18, 1999.

* cited by examiner

*Primary Examiner*—James Ketter
*Assistant Examiner*—Richard Schnizer
(74) *Attorney, Agent, or Firm*—Beth E. Arnold; John D. Quisel; Foley Hoag, LLP

(57) ABSTRACT

The present provides a mammal in which the expression of one or more interleukin genes has been suppressed. More specifically, the invention concerns the inactivating deletion of the interleukin-1 receptor antagonist gene to produce a knock-out non-human mammal with decreased or completely suppressed expression of the endogenous gene. The invention provides methods for preparing such knock-out mammals and methods of using the knock-out mammals to evaluate the effectiveness of therapeutic agents and regimens to treat diseases or disorders associated with perturbations in the interleukin pathways.

21 Claims, 6 Drawing Sheets

```
   1 GGATCTGGTT TTTTTTTGGG GGGGAGGGGG ATCGGGACAG GGGGATCAGC AAATAGACTC
  61 GGAGTACCTG TCATGCAAAT GAGGGAGTCT GGTTTTCATT GTGCTCTTCT TCCCAGGAAC
 121 ACCATGAAGG GGAAACAGAG AACTTAATTT TGGGGAAATT ACACAGGGTA AGGGGGAGGA
 181 GATCAGTTAC AACACACCAT TGCGACACTT TCAGGGTTGA CAGCGACAGC AGTAAAGGTT
 241 TCTCTTTTTG GAAATATGAG GGTTTTTCCG CTTCTGACAG TGGAACGGAA TGACAGCAGC
 301 ACAGGCTGGT GAATGACTAC TTTCTTTATA AGCAACCACC TTGAGCCTGA AATGGCAGTC
 361 GCTAGTCTCT ATTGCCTTGC TGTGGCCTCG GGATGGAAAT CTGCTGGGGA CCCTACAGTC
 421 ACCTAATCTC TCTCCTTCTC ATCCTTCTGT TTCATTCAGA GGCAGCCTGC CGCCCTTCTG
 481 GGAAAAGACC CTGCAAGATG CAAGCCTTCA GGTAAGTCTT CCAAAGACAC AGGATTGCAT
 541 AGACCAAGGA CCAGAGACAC ATGCCATATG TCCAGAGCAT ATGCAGGAAT AGGAGATATA
 601 TATACATGTA ATATATATAT AATGCGTGTG TGTATGTGTG TATACACATA TGTATGTATG
 661 TATGTGTATA TATATATATA TATATATAAT GTGTGTGTAT ACACATATGT ATGTATGTGT
 721 ATATATATAT ATATATATAT GTGTGTGTGT GTGTGTGTGT GTGTGTATCC TTGATTCAAG
 781 AACAGCATGC TAAATGCAGT CTTTAAGTCT TATGTTTTAA AATATTCCAT GCATGGACAA
 841 CAAGACAGTT AACTGTGCTC ACTTTCTCAG ACACCTAGAT GTTCAGTAAG TGATGGACAG
 901 GCATCCGGGA ATAATGCTAG CTTTGGGATC GAGCAAAGAG GAATACTTCA GCAGGACACA
 961 GTCAAAGGCT CAGACCAACA GTCTACACTC TGTATCTGTG TTGACTTGGA AGATATCTCT
1021 CGTTGGAGTC CCCAGTTTCC TTATCTGTAA CATGATACTG CTCTGATGAT AACCCCTTGT
1081 GTGCCTTACA GGGTGAACAC TAAATACATG AGTGATACTG TAACCATGTT CTGAGACCTA
1141 TGCTCTGAGA ACTGTAAAGT GCCTGAAAAA TAACCTGAGT TTTAAAAATT GGATCAAAAG
1201 CCTTGGGAGA TGCCATCAAC CTTATAGTAA AAATGGCAGG CCTCGATTTT GATTTTAAAA
1261 TGAATAAAGA GATTGTTGGT GCATATGATC TGTTCTTGAT CCTTCCTGAG AGTGAAGTCT
1321 GTGTTGAGTC ACTTCCCCTT TGACCCTGTC TGCTTTGGAT CCACAGCTGG AGGCTGGGAC
```

Fig. 1A

1381 TCTAACTGTG ATTCTATACA TCTATCCCAA GGCAAGTCTG TCCCACAGAT CCAGTAACTG
1441 CTTCGTGAGA TTTACCATCA TCACATCCTC TTAGCAGCCT CAAGAGAGGT CCCTGGAGTC
1501 CTGTTAGCAA GACTATTGAC TCCCTAGACT TTGAAGCTCA CCAGAGATAT AGACACCAGT
1561 CACAAAGGCA CAAATACTCT TTCACGTGCA GAGTACTTGG TTTGTCCTCC ACCCATCCCT
1621 GAGCTCCTAG GCTGCTCCAA GCTACTCAAA AAGTCCTGTC AGCTCTGCTG ACCAGGTAAA
1681 GAGATAAGGG ACAGATCCAA GGTCATATCA TCAGGCCTCT TACCACACCT CACAGGTGCC
1741 TGCCTCTCTG GAAGCCAGAG GGCCTTTCAC CAAGAAGTCA GAGAGTAACA AACAGGCCCT
1801 GGCTGAGCTA GACAGGAAGC TGACTTATTT CCAAGGACAG CTGTCCCTGT CAGGCCCAGA
1861 GCAGATGGTC CCACAAGAGG TTTTAGTTGT AGACTTGCAG GTCTAAGTAG AGTAGCTTGA
1921 GGTAGGAGTA GTGAAGCCAG ACTAGCTTGG CTACAATACA TTCTAACCCT TGAACCTGTA
1981 ACACTATGAT GTGGTGGCCA CGAGCTACAA GTGGCCATCT AAATTTACAC ATAAACGCAT
2041 GAAAGCAGAA GAAAGTCCTG TACCTGGCAA CTCTATTTAG TGGAGTGACT ATAGGATGTG
2101 CTTGCATCGC CTAAGTTTCT ATCAGATGCT GACGCTCTAT AGAAAATTCT GCTAAAGTCA
2161 TGGATGTCCA TGCTGGGATT CTGAGGTGAG GAACAAGAAA AAGAGGTTTT CTGTTCACCA
2221 GATGTGAGAG ATGGGCTCAT TTCTTACATG GTATTTGCTT AAATCTTCCC ATTTGTGTTA
2281 TGAACTTGGT AAGTACGACA CTTCCAGCAA GTCTAGATGT AAATTAGGTG ACTCTGAGGA
2341 AGCTGGAAAG GGCTCTGTAC TGCCTACTCC AGCTAGGCCA TTTTGCTTTT CAGAATCTGG
2401 GATACTAACC AGAAGACCTT TTACCTGAGA AACAACCAGC TCATTGCTGG GTACTTACAA
2461 GGACCAAATA TCAAACTAGA AGGTGAGTGG ATAACAGGGA AGCTGGTGTA ATATGGACAT
2521 AGAGTCCTTT GCCCTGCTCC TCTGCCTGGA GGTGGGATGT CCTCATTTCT GTTGAGTTGG
2581 AAATGAGAGA TTTGACCACC AGGGGACATA TGGGAGTGGC CTCAAGAGAG CAGAAAAGAT
2641 AAAGACTGGG TCACAATGCT CCAGGGACAC AGCTGAGAGG AACAGAGGCC AGAAGGCACC
2701 CGGGCACCTC CTTAGTCCTT CTGTGCTGGT AGTCCACTAT ACCCCAGTGT TATTCGAACT
2761 CTACCCTTGC CCTAGGCTAA TATAACATGT ATGTGGGCTG GGTAGCATTT TTACTGTGGA
2821 CACCACCCTC ATCATGTACC CTCTAAACTA GGACAAAGCC ACATGAACTT GGAGGAGCAT
2881 TACCCACAGA TTCTTCAGTT TTTCTTAGTT CAGGCACTTA GTTGACAGAA TCTCTGTTTG

Fig. 1B

2941 TGAGGGAACG AAGCATTACT TGTATCTCCT CAGGATCCCC CAAGCCTTCT CCTTTCCTGT
3001 ATCACTCAGC AGTTATGCAA CTGGCTTTTC CTGTCTTTCT AGTAATTCTC CCATGAACAC
3061 ACTCAAGCAT AGAAGGTGCT GGCTTTCTAT TGCTACCCAG TAACAGGATG GAAACGTGAA
3121 CTGTGTGGAA CCTATTCATG CGCCTTCTGA GCTTTTGTGC CTCTGTCTAC TAACAGCAAA
3181 TCTGTTGACT TGGAGGTCTG GTTCACTCTA GAAAGTAAAG GAAAGTTGGG AGCAGTGTAG
3241 AATCTAGGAA GCTGGTCCTT ACATAGAGTG TGCTCATTTG GATCTTTTGC TTGGAGGCAG
3301 ACTAGAAAGA TAGAGCCTTC TTGACCTTCT TGACCTTCTA GTTTTATAAA AAGGAAGACA
3361 GAAAATACAC ACAGACGCTC CCCTACCCTT GCCTCCTCTT CTCTCTTTCT GACACCATCC
3421 TCTACTCTTC TCCAGAAAAG ATAGACATGG TGCCTATTGA CCTTCATAGT GTGTTCTTGG
3481 GCATCCACGG GGGCAAGCTG TGCCTGTCTT GTGCCAAGTC TGGAGATGAT ATCAAGCTCC
3541 AGCTGGAGGT AAGAATCTGG TTTAGCTATC AAATCCTTCT AAAACCCAAT GGTTATGACA
3601 ACCTCAGGTG TTTCTCATAA CCCTGAGCAT GCAAAGATGA GGGAGGCTTT TCCTTCTTCA
3661 CAGAGTACTA TTTTGAGGTC ACTCCTTAAG CAGTTTCCAC AATGTTCTTG GTTGATATTG
3721 GGTGTCCAAG GTGGTTTCTC ATTCTCTCAA CTACCCTTTA CGTAACTTCT TTGCATTCAG
3781 TCAACACTCT GAGCTTCCTT AAGCGTGGTG ACCAACTTTT ATGAGAGATT GTTCCAGAAA
3841 GATGAGCCTC AATGTGAAAG TGCTTATTAA GCTTGGGCTT ATGTAAGTCT ATTGGCAGAA
3901 GCCTGTGACG TGGTTGATAT GGACTCATTG TAGAAAGGTA CTGCACAAGG ATCTAAACTT
3961 TAGGAGGAGA CATGGTCATT AGAGGAGCAC GACCTGAACC ACCATGGGTC TTGTGCCTCC
4021 TAAACCAGTT GAGCCTACCT TCTTCTAGCA AGGTCAATTC TCAAGACTAT ACACTCCCAA
4081 GCATCATCTA TGCTATTTAT TATCTACGCT CCTAATTTAC ATCCCACACA GACCTGTGTC
4141 ACTTACTCCT TTACCTAGTC AGTAGTAATG GGCTGTTCAA ACATTATCTT GAGGGATTAG
4201 CTGGACAAAC TTTTAATCCA ACTGCAAATA GCCACAAGCA TGAGTTTGTT GATAACTCTT
4261 ACCAATGGAC AGGAACACCT TTTAGAGGAC TTTCTCAGCC CTCGGCAATT ACCTGACCAT
4321 TTCTTGACTT CCAGGAAGTT AACATCACTG ATCTGAGCAA GAACAAAGAA GAAGACAAGC
4381 GCTTTACCTT CATCCGCTCT GAGAAAGGCC CCACCACCAG CTTTGAGTCA GCTGCCTGTC
4441 CAGGATGGTT CCTCTGCACA ACACTAGAGG CTGACCGTCC TGTGAGCCTC ACCAACACAC

Fig. 1C

```
4501 CGGAAGAGCC CCTTATAGTC ACGAAGTTCT ACTCCAGGA AGACCAATAG TACTGCCGAG
4561 GCCTGTAATA ATCACCAACT GCCTCATCAC TCTGGCCATC ATTGGGGCCT GAGGAACAAC
4621 TTTTGCAGGG TGTACAGTAG AAGCAGACAG AAGAGTTCTG ATGATAGATC TCTGCCTCAG
4681 TCTGTTGGCT GGCCTAATCC CCATGATGAT TCCAGAATAA TCTTGCAAAT TGGATCATGG
4741 CAGGTGCTTG TTCAAAGCCC TTTCTTGTTG CCTCTGCCAT CTGGGTGAAG TCTAGACCAC
4801 TTGCTTGGCC TAGGTGTCTT CTGCTCTACC ACCCACCCTA CCCCTGCCAC AAACACACAC
4861 TTTTTTTGTT TTTGTTTTTT CCATTGTTCT GCACTTCCAC AGTCCAGACC AATCAAGTCA
4921 CTTGACAATA TGCCCCAAGT GACTCCCTTA CCCTGTTTTA TAAACCTGTG CCTGTCTATG
4981 GAGAAGGTTT TAATTCTCCT TGTTATTCAT TTTGGGCTTT TTGATGAAAC CACCAGGGCA
5041 TCACATATAC TAAGCATGTG CTCTACCATC ATGTTATGCT TCCAGCTCAG GGGGGCACTT
5101 TTAAGGATCT AGAAAACAGA AATTAAGGAT CTCATAGTTA TTTTATTAGG CCAGCCTTAT
5161 TCCATGTCGG CAAGAGGTTT CTTGTGGAAA TTATGTCCTT TCTGAGAGGA GCTGGGGATT
5221 AGATGCTCCT GCATTTGTGA AATGGTTATA AGCATAGAAA AATAGGTGGT AAGCTTTCCT
5281 TCTTTCCTTA TTTTGTGTGA TGCCTTAAAC TGAAAAGTTA AAAATTGATG GATTGTAGCA
5341 TTCCCATAAT CTCCCCCTTC TTTTTTTTTC CTTTGGAAAT GTCCAATAGT CTATATTCCT
5401 CTGTCCCGCC CAAACACCAT CTTCACTCCA AGCCTACCAC AGATGCCTGA AGAAGTTCCT
5461 CACTATCTGC AAATGTGGCT CTCAGGCCCT TCCTGATGTG ATGAATGAAT CTACTAATCA
5521 TTTCTTGACC GTTCATTTTA TCACTTCTAA CCTTGAAACA TGTGGAAGTA GCTATGTTCC
5581 TAACTGTTTC CTCTGCCAGA CAATGAACTC TGGAGATCAG GGAGCTTCGT GTGTGTGT
5641 GTGTGTGTGT GTGTGTGTGT GTGTGTGTGT GCGCGCGCGC ACGTGCATGC ACATGCTACG
5701 TATTGGGTCC CTCCAAGGAT GAACCCTCTC TTTGGCTTAG AAGGCACTCA GAGAATATGT
5761 GTTATTCGTG CTCACGGAAA GTTTCTTACT CATCCCTGTG ACTTTGGCTT TATTTTACAA
5821 TAAAACACTG AAAATGTCCA CTTTGTTAGT TGTGAACATG AGCCCAGGCC TAAGGTGCTG
5881 GGAAACAGAA AGGGCGGGAG ATTTTTCTTT ATTCTATGGC TAGAAAATAG TTACCTCCT
5941 TCTGAAAGTC TTCTTCCTCA TTTCTGGGTA ACAGAATATC AAACACCTTG CTTATAAGTT
6001 ATAAAGTAGT GTTGTCCACC ATGAACCCAC CAAGTAAAAA CAACCCAAAT ACCTATCATG
```

Fig. 1D

```
6061 GATGAATAAT CATGCAAGTA TCAGATCTGC ACTCAATGCC ACACAATGAC AAAGATAGCA
6121 AATGAGCCAC AGACGGCTCC ACCCAACCCA ATAGATGAAC ACTTGGTTCA AAATCACTAA
6181 AGCTCAAATA CTCCCAGGTC AAACACCAGG TAACAAGTTA ATACTCAACA AAGGGGGGAA
6241 ACAAATGTTC CACTGAATCC TGTGACCCTG TGGCGTGGTT CACCTCCTGT GTTGTTTGCC
6301 ATGTGTGCTC AGGATGAGCT GATTAAAGCT CTTCTCAGGG GTTCAGTTTT
```

Fig. 1E

```
   1  GCCTTCCCCA GTCAGGCAAG AAGCAGCAAG GTACAAGAAT ACACAGCTCC AGGCTCCAAG
  61  GGTCCTGTCC GCTCAGGAAG TTGTTGCGGA CAATGTTCAT CTTGCTTGTG TTAGTAACTG
 121  GAGTTTCTGC TTTCACCACT CCAACAGTGG TGCACACAGG AAAGGTTTCT GAATCCCCCA
 181  TTACATCGGA GAAGCCCACA GTCCATGGAG ACAACTGTCA GTTTCGTGGC AGAGAGTTCA
 241  AATCTGAATT GAGGCTGGAA GGTGAACCTG TGGTTCTGAG GTGCCCCTTG GCACCTCACT
 301  CCGACATCTC CAGCAGTTCC CATAGTTTTC TGACCTGGAG TAAATTGGAC TCTTCTCAGC
 361  TGATCCCAAG AGATGAGCCA AGGATGTGGG TGAAGGGTAA CATACTCTGG ATTCTGCCAG
 421  CAGTGCAGCA AGACTCTGGT ACCTACATTT GCACATTCAG AAACGCATCC CACTGTGAGC
 481  AAATGTCTGT GGAACTCAAG GTCTTTAAGA ATACTGAAGC ATCTCTGCCT CATGTCTCCT
 541  ACTTGCAAAT CTCAGCTCTC TCCACCACCG GGTTACTAGT GTGCCCTGAC CTGAAAGAAT
 601  TCATCTCCAG CAACGCTGAT GGAAAGATAC AGTGGTATAA GGGCGCCATA CTCTTGGATA
 661  AAGGCAATAA GGAATTTCTG AGTGCAGGAG ACCCCACACG CCTATTGATA TCCAACACGT
 721  CCATGGACGA TGCAGGCTAT TACAGATGTG TTATGACATT TACCTACAAT GGCCAGGAAT
 781  ACAACATCAC TAGGAATATT GAACTCCGGG TCAAAGGAAC AACCACGGAA CCCATCCCTG
 841  TGATCATTTC TCCCCTGGAG ACAATACCAG CATCATTGGG GTCAAGACTG ATAGTCCCGT
 901  GCAAAGTGTT TCTGGGAACT GGTACATCTT CCAACACCAT TGTGTGGTGG TTGGCTAACA
 961  GCACGTTTAT CTCGGCTGCT TACCCAAGAG GCCGTGTGAC CGAGGGGCTA CACCACCAGT
1021  ACTCAGAGAA TGATGAAAAC TATGTGGAAG TGTCGCTGAT TTTTGATCCA GTCACAAGGG
1081  AGGATCTGCA TACAGATTTT AAATGTGTTG CCTCGAATCC ACGGAGTTCT CAGTCACTCC
1141  ATACCACAGT CAAAGAAGTC TCTTCCACGT TCTCCTGGAG CATTGCGCTG GCACCTCTGT
1201  CTCTGATCAT CTTGGTTGTG GGGGCAATAT GGATGCGCAG ACGGTGTAAA CGCAGGGCTG
1261  GAAAGACATA TGGACTGACC AAGCTACGGA CTGACAACCA GGACTTCCCT TCCAGCCCAA
1321  ACTAAATAAA GGAAATGAAA
```

Fig. 2

TRANSGENIC MODELS OF INFLAMMATORY DISEASE

BACKGROUND OF THE INVENTION

IL-1 Genes in Disease

The IL-1gene cluster is located on the long arm of human chromosome 2 (2q13) and contains at least the genes for IL-1α (IL1A), IL-1β (IL1B), and the IL-1 receptor antagonist (IL-1RN) within a region of 430 Kb (Nicklin, et al., *Genomics* 19:382–4 (1994)). The agonist molecules, IL-1α and IL-1β, have potent pro-inflammatory activity and initiate many inflammatory cascades. The IL-1α and IL-1β proteins are less than 30 per cent homologous to each other, but both species bind to the same cell surface receptors and their biological activities as cytokines appear to be similar. IL-1 cytokine activity is antagonized by two naturally-occurring inhibitors—the IL-1 receptor antagonist, and the IL-1 type II receptor. The IL-1 receptor antagonist is structurally homologous to IL-1α and IL-1β and binds to IL-1 type I receptors but is biologically inactive, so that it functions as a competitive inhibitor of IL-1. In contrast, the interleukin-1 type II receptor antagonizes IL-1 action by competitively inhibiting IL-1 binding to the type I receptor. In certain cell types, IL-1 receptor antagonist mRNA is spliced to remove the signal sequence so it is not secreted, but the function of intracellular IL-1 receptor antagonist is not known.

The IL-1 receptor antagonist and IL-1 type II receptors appear to play important roles as naturally-occurring antagonists of IL-1 function. Inappropriate production of IL-1 appears to play a central role in the pathology of many autoimmune and inflammatory diseases, including rheumatoid arthritis, inflammatory bowel disorder, Type I diabetes, and psoriasis. IL-1RN allele 2 is associated with osteoporosis (U.S. Pat. No. 5,698,399), nephropathy in diabetes mellitus (Blakemore, et al., *Hum. Genet.*, 97:369–74 (1996)), alopecia areata (Cork, et al., *J. Invest. Dermatol.*, 104(5 Supp.): 15S–16S (1995)), Graves disease (Blakemore, et al., *J. Clin. Endocrinol.*, 80(1): 111–5 (1995)), systemic lupus erythematosus (Blakemore, et al., *Arthritis Rheum.*, 37:1380–85 (1994)), lichen sclerosis (Clay, et al., *Hum. Genet.*, 94:407–10 (1994)), and ulcerative colitis (Mansfield, et al., *Gastoenterol.*, 106(3):637–42 (1994)).

Furthermore, still other diseases and conditions have been associated with IL-1 fimction through the identification of specific human polymorphisms which are associated with an increased risk for developing these diseases and conditions. For example, coronary artery disease (PCT/US98/04725), is associated with IL-1B (-511) allele 2 and IL-1RN (VNTR) allele 2. Diabetic retinopathy (PCT/GB97/02790) is associated with IL1-RN (VNTR). Low birth weight, pregnancy complications and severe periodontal disease (U.S. Pat. No. 5,686,246) are associated with IL-1A (-889) allele 2 and IL-1B (3954) allele 2. The IL-1B (3954) allele 2 is associated with psoriasis and insulin dependent diabetes in DR3/4 patients (di Giovine, et al., *Cytokine* 7: 606 (1995); Pociot, et al., *Eur J. Clin. Invest.* 22: 396–402 (1992)). In addition, there are stable inter-individual differences in the rates of production of IL-1, and some of this variation may be accounted for by genetic differences at IL-1 gene loci (Molvig, et al., *Scand J. Immunol.*, 27:705–16 (1988); Pociot, et al., *Eur. J. Clin. Invest.*, 22:396–402 (1992)). Furthermore allele 2 of IL-1RN (VNTR) is associated with ulcerative colitis in Caucasian populations from North America and Europe (Mansfield, J. et al., (1994) Gastroenterology 106: 637–42), particularly within populations of ethnically related Ashkenazi Jews (PCT WO97/25445). Thus, the IL-1 genes are likely mediators of many inflammatory diseases.

Inflammation is now generally regarded as an important component of the pathogenic process of atherosclerosis (Munro, *Lab Invest.*, 58:249–261 (1988), Badimon, et al., *Circulation*, 87:3–16 (1993), Liuzzo, et al., *N.E.J.M.*, 331 (7):417–24 (1994), Alexander, *N.E.J.M.*, 331(7):468–9 (1994)). Several inflammatory products, including IL-1β, have been identified in atherosclerotic lesions or the endothelium of diseased coronary arteries (Galea, et al., *Ath. Thromb. Vasc. Biol.*, 16:1000–6 (1996)). Also, serum concentrations of IL-1β are elevated in patients with coronary disease (Hasdai, et al., *Heart*, 76: 24–8 (1996)). Although it was historically believed that the presence of inflammatory agents was responsive to injury or monocyte activation, it is now thought that an abnormal inflammatory response may be causative of coronary artery disease or create an increased susceptibility to the disease. Indeed, particular IL-1RN and IL-1B alleles have been found to be overrepresented in patients with CAD (PCT/US98/04725).

Transgenic Animal Models

There are two basic types of animals with genetically manipulated genomes. A traditional transgenic mammal has a modified gene introduced into its genome and the modified gene can be of exogenous or endogenous origin. A "knockout" mammal is a special type of transgenic mammal, characterized by suppression of the expression of an endogenous gene through genetic manipulation. The disruption of specific endogenous genes can be accomplished by deleting some portion of the gene or replacing it with other sequences to generate a null allele. Cross-breeding mammals having the null allele generates a homozygous mammals lacking an active copy of the gene.

A number of such mammals have been developed, and are extremely helpful in medical development. For example, U.S. Pat. No. 4,736,866 describes a mouse containing a transgene encoding an oncogene. U.S. Pat. No. 5,175,383 describes a mouse with a transgene encoding a gene in the int-2/FGF family. U.S. Pat. No. 5,616,491 describes knock-out mice having suppression of CD28 and CD45. Furthermore, U.S. Pat. No. 5,824,837 describes a transgenic mouse that expresses a human IL-1B transgene. This transgenic mouse is useful for studying specific inflammatory processes mediated by IL-1. Similarly WO 9723129 describes a transgenic animal expressing IL-1a which can be used in research and development of remedies for inflammatory processes mediated by IL-1a.

Transgenic animal models of IL-1 mediated inflammatory diseases would be very useful for identifying pharmaceutical agents that are able to treat or prevent inflammatory diseases.

SUMMARY OF THE INVENTION

In one aspect, the invention provides transgenic non-human organisms and cell lines for use in the in vivo screening and evaluation of drugs or other therapeutic regimens useful in the treatment of inflammatory disorders. In one embodiment, the invention is a transgenic animal with a targeted disruption in an interleukin-1 gene. In particular, the gene is the IL-1RN gene. The animal may be chimeric, heterozygotic or homozygotic for the disrupted gene. Homozygotic knock-out IL-1RN mammals have a strong tendency towards developing an inflammatory condition, such as rheumatoid arthritis, inflammatory bowel disorder, Type I diabetes, psoriasis, osteoporosis, nephropathy in diabetes mellitus, alopecia areata, Graves disease, systemic lupus erythematosus, lichen sclerosis, ulcerative colitis, coronary artery disease, arteritic disorders, diabetic retinopathy, low birth weight, pregnancy complications, severe periodontal disease, psoriasis and insulin dependent diabetes, but is particularly characterized by arteritic lesions. The targeted disruption may be anywhere in the gene, subject only to the requirement that it inhibit production of functional IL-1ra protein. In a preferred embodiment, the disruption occurs from the EcoRV site in exon 3 to the first XbaI site in exon 4 of the wild type gene. The transgenic animal may be of any species (except human), but is preferably a mammal. In a preferred embodiment, the non-human animal comprising a targeted disruption in the interleukin-1 receptor antagonist gene, wherein said targeted disruption inhibits production of wild-type interleukin-1 receptor antagonist so that the phenotype of a non-human mammal homozygous for the targeted disruption is characterized by an inflammatory condition.

In another aspect, the invention features a cell or cell line, which contains a targeted disruption in the interleukin-1 receptor antagonist gene. In a preferred embodiment, the cell or cell line is an undifferentiated cell, for example, a stem cell, embryonic stem cell, oocyte or embryonic cell.

Yet in a further aspect, the invention features a method of producing a non-human mammal with a targeted disruption in an interleukin-1 gene. For example, an IL-1RN knock-out construct can be created with a portion of the IL-1RN gene having an internal portion of said IL-1RN gene replaced by a marker. The knock-out construct can then be transfected into a population of embryonic stem m(ES) cells. Transfected cells can then be selected as expressing the marker. The transfected ES cells can then be introduced into an embryo of an ancestor of said mammal. The embryo can be allowed to develop to term to produce a chimeric mammal with the knock-out construct in its germline. Breeding said chimeric mammal will produce a heterozygous mammal with a targeted disruption in the IL-1RN gene. Homozygotes can be generated by crossing heterozygotes.

In another aspect, the invention features IL-1RN knock-out constructs, which can be used to generate the animals described above. In one embodiment, the IL-1RN construct can comprise a portion of the interleukin-1 receptor antagonist (IL-1RN) gene, wherein an internal portion of said IN-1RN gene is replaced by a selectable marker. Preferably, the marker is the neo gene and the portion of the IL-1RN gene is at least 2.5 kb long or 7.0 or 9.5 kb long (including the replaced portion and any IL-1RN flanking sequences). The internal portion preferably covers at least a portion of an exon and most preferably it is from the EcoRV site of exon 3 to the XbaI site of exon 4.

In still another aspect, the invention features methods for testing agents for effectiveness in treating and/or preventing an inflammatory condition. In one embodiment, the method can employ the transgenic animal or cell lines, as described above. For example, a test agent can be administered to the transgenic animal and the ability of the agent to ameliorate the inflammatory condition can be scored as having effectiveness against said inflammatory condition. Any inflammatory condition with an IL-1 component can be tested using these mammals, but in particular, conditions characterized by arteritic lesions are studied. The method may also be used to test agents that are effective against the IL-1 inflammatory proteins and their downstream components.

BRIEF DESCRIPTION OF THE DRAWINGS

FIG. 1 shows the DNA sequence of the mouse IL-1 receptor antagonist (IL-1RN) gene (GenBank Acc. No. L32838) (SEQ ID NO:1).

FIG. 2 shows the exonic DNA sequence of the mouse IL-1 type II receptor gene (GenBank Acc. No. X59769) (SEQ ID NO:2).

DETAILED DESCRIPTION OF THE INVENTION

4.1 General

In general, the invention provides transgenic animals in which one or more IL-1 related genes have been modified by transgenic cloning procedures. These IL-1 transgenic animals are useful as animal models for various diseases which involve IL-1 mediated inflammatory processes. Although most of the above described inflammatory diseases and conditions appear to have a complex and multifactorial etiology, they all appear to ultimately involve IL-1 mediated inflammatory processes. The present invention also provides reagents and methods for the discovery of pharmaceutical compounds which are able to interfere with these IL-1 mediated inflammatory processes and thereby block the progression of these otherwise disparate diseases.

In a preferred embodiment, the invention features a transgenic "knock-out" mouse line in which the mouse IL-1RN (interleukin-1 receptor antagonist) gene carried on mouse chromosome 2 at position 10.0 cM (Mouse Genome Informatics, www.informatics.jax.org/) is disrupted or deleted so as to decrease or eliminate expression of the IL-1RN gene. In another embodiment, the invention features a transgenic "knock-out" mouse line in which the mouse IL-1 type II receptor (decoy receptor) gene carried on mouse chromosome 1 at position 19.5 cM (Mouse Genome Informatics, www.informatics.jax.org/) is disrupted or deleted so as to decrease or eliminate expression of the IL-1 type II receptor. The IL-1RN and IL-1 type II receptor knock-out mouse lines both feature an enhancement of IL-1 cytokine-mediated inflammatory processes due to loss of an endogenous IL-1 antagonist molecule. In a more preferred embodiment, the invention provides a "double" knock-out mouse line featuring decreased expression of both the IL-1RN gene and the IL-1 type II receptor antagonist gene.

The transgenic "knock-out" mouse line is useful to generate both heterozygous and homozygous IL-1 antagonist gene knock-out mice which can be used to study IL-1 mediated inflammatory diseases and conditions. For example, loss of the IL-1 receptor antagonist ligand leads to hyperactivity of IL-1 mediated inflammatory processes, and this hyperactivity of IL-1 mediated processes contributes to the etiology of a number of disesases and conditions including: rheumatoid arthritis, inflammatory bowel disorder, Type I diabetes, psoriasis, osteoporosis, nephropathy in diabetes mellitus, alopecia areata, Graves disease, systemic lupus erythematosus, lichen sclerosis, ulcerative colitis, coronary artery disease, arteritic disorders, diabetic retinopathy, low birth weight, pregnancy complications, severe periodontal disease, psoriasis and insulin dependent diabetes, and arteritic lesions.

Both chronic and acute forms of such inflammatory diseases and conditions can be reproduced in appropriate IL-1RN knock-out animals or animal lines. For example, animals heterozygous for the IL-1RN knock-out construct have diminished capacity to produce the interleukin-1 receptor antagonist and therefore show a corresponding accentuation of IL-1 mediated inflammatory processes. The heterozygous mouse lines may therefore reproduce the circumstances of chronic inflammatory diseases and conditions. Furthermore, these heterozygous animals or cell lines are well suited to finding therapeutic agents which act to accentuate the expression or activity of the diminished pool of endogenous IL-1 receptor antagonist. Such receptor antagonist "agonists" may, for example, increase expression of the remaining copy of the IL-1RN gene. In contrast, homozygous IL-1RN "knock-out" animals and lines have no ability to produce the IL-1RN gene product and hence show a correspondingly large enhancement of IL-1RN mediated processes. The homozygous animals and cell lines may therefore reproduce the aberrant immune functions which occur is acute inflammatory diseases. Furthermore, these homozygous animals and lines are well suited to finding therapeutic IL-1RN agonists which function, for example, as molecular mimics of the interleukin-1 receptor antagonist by, for example, binding to interleukin-1 a and/or interleukin-1 b and preventing their interaction with an interleukin receptor.

The invention further provides various nucleic acid constructs useful for creating IL-1RN "knock-out" and IL-1RN "knock-in" transgenic mouse cell lines and transgenic mice.

For example, an IL-1RN disrupting construct can be engineered so as to incorporate a reporter or marker gene (such as beta-galactosidase or green fluorescent protein) into a chromosomal copy of the gene, thereby rendering the resulting chimeric reporter gene dependent upon the endogenous IL-1RN gene promoter for its expression. Transgenic cell lines and animals incorporating such "knock-in" constructs are particularly well suited to the screening of compounds for their ability to suppress IL-1 dependent inflammatory processes by increasing the transcription of the IL-1 receptor antagonist gene. In another example, an heterologous regulatable promoter can be "knocked-in" to the IL-1RN gene locus so that IL-1 receptor antagonist expression is now controlled by the regulatable promoter. The regulatable promoter can be an inducible promoter, a repressible promoter or a developmentally regulated promoter. The choice of promoters in this instance can be tailored to the specific study at hand. For example, a repressible promoter system, such as provided by certain derivatives of the tetracycline repressor and corresponding operator sequence (see Gossen et al. (1995) Science 268: 1766–9), facilitates the production of mouse lines in which the IL-1RN gene is expressed until some point in time after normal growth and development. The function of the IL-1RN gene can then be abruptly halted by administration of an appropriate ligand (such as tetracycline) which results in the transcriptional shut-down of the IL-1RN gene. This inducible IL-1 receptor antagonist deficiency thereby triggers IL-1 mediated inflammatory conditions in an otherwise normally developing animal. Pharmaceutical screens can thus be devised for compounds capable of blocking an IL-1 receptor antagonist deficiency-induced inflammatory response. In other embodiments, a tissue-specific promoter element can be "knocked-in" to the IL-1RN gene. The resulting animal will not produce IL-1 receptor antagonist in any body tissues in which the tissue-specific promoter is not expressed. Such a transgenic animal is particularly useful for the study of inflammatory processes affecting a specific set of tissues. Pharmaceutical screens can thus be devised for compounds capable of blocking the IL-1 receptor antagonist deficiency-induced inflammatory responses which occur in the non-expressing tissues. In a similar embodiment, the cre/lox transgene displacement system can be used to design receptor antagonist knock-in construct which are susceptible to genetic deletion in somatic tissue following expression of the Cre recombinase protein. The transgenic expression of Cre recombinase by a tissue-specific and/or inducible promoter thereby allows for a spatially and/or temporally targeted loss of the IL-1RN gene. This method can be used, for example, to produce mice in which there is a tissue-specific depletion of IL-1 receptor antagonist and a corresponding tissue-specific activation of inflammatory processes. Thus these transgenic mouse lines can be used to study IL-1 mediated inflammatory diseases which affect a specific tissue or tissues and at a specific time in the life of the organism. Pharmaceutical screens can be employed with such transgenic mice in order to discover compounds which treat or prevent analogous tissue-specific inflammatory diseases in humans.

The IL-1 transgenic animals and cell lines of the present invention may thus be used for the development of pharmaceutical agents which are useful for treating or preventing such IL-1 mediated diseases and conditions.

4.2 Definitions

For convenience, the meaning of certain terms and phrases employed in the specification, examples, and appended claims are provided below.

The term "agonist", as used herein, is meant to refer to an agent that mimics or upregulates (e.g. potentiates or supplements) an IL-1 bioactivity. An IL-1 agonist can be a wild-type IL-1 protein or derivative thereof having at least one bioactivity of the wild-type IL-1, e.g. receptor binding activity. An IL-1 therapeutic can also be a compound that upregulates expression of an IL-1 gene or which increases at least one bioactivity of an IL-1 protein. An agonist can also be a compound which increases the interaction of an IL-1 polypeptide with another molecule, e.g, an interleukin receptor. Agonists can be any class of molecule, preferably a small molecule, including a nucleic acid, protein, carbohydrate, lipid or combination thereof.

"Antagonist" as used herein is meant to refer to an agent that downregulates (e.g. suppresses or inhibits) at least one IL-1 bioactivity. An IL-1 antagonist can be a compound which inhibits or decreases the interaction between an IL-1 protein and another molecule, e.g., a receptor, such as an IL-1 receptor. Accordingly, a preferred antagonist is a compound which inhibits or decreases binding to an IL-1 receptor and thereby blocks subsequent activation of the IL-1 receptor. An antagonist can also be a compound that downregulates expression of an IL-1 locus gene or which reduces the amount of an IL-1 protein present. The IL-1 antagonist can be a dominant negative form of an IL-1 polypeptide, e.g., a form of an IL-1 polypeptide which is capable of interacting with a target peptide, e.g., an IL-1 receptor, but which does not promote the activation of the IL-1 receptor. The IL-1 antagonist can also be a nucleic acid encoding a dominant negative form of an IL-1 polypeptide, an IL-1 antisense nucleic acid, or a ribozyme capable of interacting specifically with an IL-1 RNA. Yet other IL-1 antagonists are molecules which bind to an IL-1 polypeptide and inhibit its action. Such molecules include peptides, e.g., forms of IL-1 target peptides which do not have biological activity, and which inhibit binding by IL-1 to IL-1 receptors. Thus, such peptides will bind the active site of IL-1 and prevent it from interacting with target peptides, e.g., an IL-1 receptor. Yet other IL-1 antagonists include antibodies interacting specifically with an epitope of an IL-1 molecule, such that binding interferes with the biological function of the IL-1 locus polypeptide. In yet another preferred embodiment, the IL-1 antagonist is a small molecule, such as a molecule capable of inhibiting the interaction between an IL-1 polypeptide and a target IL-1 receptor. Alternatively, the small molecule can function as an antagonist by interacting with sites other than the IL-1 receptor binding site.

The term "allele", which is used interchangeably herein with "allelic variant" refers to alternative forms of a gene or portions thereof Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. Alleles of a specific gene can differ from each other in a single nucleotide, or several nucleotides, and can include substitutions, deletions, and insertions of nucleotides. Frequently occurring sequence variations include transition mutations (i.e. purine to purine substitutions and pyrimidine to pyrimidine substitutions, e.g. A to G or C to T), transversion mutations (i.e. purine to pyrimidine and pyrimidine to purine substitutions, e.g. A to T or C to G), and alteration in repetitive DNA sequences (e.g. expansions and contractions of trinucleotide repeat and other tandem repeat sequences). An allele of a gene can also be a form of a gene containing a mutation. The term "allelic variant of a polymorphic region of an IL-1 gene" refers to a region of an IL-1 locus gene having one or several nucleotide sequence differences found in that region of the gene in other individuals.

As used herein, the phrase "arterial disease having an inflammatory component" or "arteritic disease" refers to the constellation of arterial diseases characterized by sclerosis. These include, but are not limited to, coronary artery disease and stroke.

"Biological activity" or "bioactivity" or "activity" or "biological function", which are used interchangeably, for the purposes herein means an effector or antigenic function that is directly or indirectly performed by an IL-1 polypeptide (whether in its native or denatured conformation), or by any subsequence thereof Biological activities include binding to a target peptide, e.g., an IL-1 receptor. An IL-1 bioactivity can be modulated by directly affecting an IL-1 polypeptide. Alternatively, an IL-1 bioactivity can be modulated by modulating the level of an IL-1 polypeptide, such as by modulating expression of an IL-1 gene.

As used herein the term "bioactive fragment of an IL-1 polypeptide" refers to a fragment of a full-length IL-1 polypeptide, wherein the fragment specifically mimics or antagonizes the activity of a wild-type IL-1 polypeptide. The bioactive fragment preferably is a fragment capable of interacting with an interleukin receptor.

The term "an aberrant activity", as applied to an activity of a polypeptide such as IL-1, refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity. For example an aberrant polypeptide can interact with a different target peptide. A cell can have an aberrant IL-1 activity due to overexpression or underexpression of an IL-1 locus gene encoding an IL-1 locus polypeptide.

As used herein, the phrase "coronary artery disease" refers to disorders and conditions generally recognized by those skilled in the art as related to the deposition of atheroma in the large- and medium-sized arteries serving the heart. Thus, coronary artery disease means clinical syndromes (including, but not limited to, angina, myocardial infarction, unstable angina, and sudden ischemic death) which are based on the pathology of coronary artery atheroma.

"Cells", "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric polypeptide" or "fusion polypeptide" is a fusion of a first amino acid sequence encoding one of the subject IL-1 locus polypeptides with a second amino acid sequence defining a domain (e.g. polypeptide portion) foreign to and not substantially homologous with any domain of an IL-1 polypeptide. A chimeric polypeptide may present a foreign domain which is found (albeit in a different polypeptide) in an organism which also expresses the first polypeptide, or it may be an "interspecies", "intergenic", etc. fusion of polypeptide structures expressed by different kinds of organisms. In general, a fusion polypeptide can be represented by the general formula X-IL-1-Y, wherein IL-1 represents a portion of the polypeptide which is derived from an IL-1 polypeptide, and X and Y are independently absent or represent amino acid sequences which are not related to an IL-1 sequence in an organism, including naturally occurring mutants.

The phrase "nucleotide sequence complementary to the nucleotide sequence set forth in SEQ ID NO. x" refers to the nucleotide sequence of the complementary strand of a nucleic acid strand having SEQ ID NO. x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID NO. x refers to the complementary strand of the strand having SEQ ID NO. x or to any nucleic acid having the nucleotide sequence of the complementary strand of SEQ ID NO. x. When referring to a single stranded nucleic acid having the nucleotide sequence SEQ ID NO. x, the complement of this nucleic acid is a nucleic acid having a nucleotide sequence which is complementary to that of SEQ ID NO. x. The nucleotide sequences and complementary sequences thereof are always given in the 5' to 3' direction.

A "delivery complex" shall mean a targeting means (e.g. a molecule that results in higher affinity binding of a gene, protein, polypeptide or peptide to a target cell surface and/or increased cellular or nuclear uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding an IL-1 polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a polypeptide with the same biological activity.

The phrases "disruption of the gene" and "targeted disruption" or any similar phrase refers to the site specific interruption of a native DNA sequence so as to prevent expression of that gene in the cell as compared to the wild-type copy of the gene. The interruption may be caused by deletions, insertions or modifications to the gene, or any combination thereof.

The term "haplotype" refers to a set of alleles that are inherited together as a group (are in linkage disequilibrium). As used herein, haplotype is defined to include those haplotypes that occur at statistically significant levels ($p_{corr} \leq 0.05$). As used herein, the phrase "an IL-1 haplotype" refers to a haplotype in the IL-1 locus.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences. An "unrelated" or "non-homologous" sequence shares less than 40% identity, though preferably less than 25% identity, with one of the IL-1 locus sequences of the present invention.

"Inflammatory disease" as used herein, refers to a disease or disorder that occurs in an individual due to tissue damage, regardless of the cause or etiology. This tissue damage can result from microbial invasion, autoimmune processes, tissue or organ allograft rejection, neoplasia, idiopathic diseases or such injurious external influences as heat, cold, radiant energy, electrical or chemical stimuli, or mechanical trauma. Whatever the cause, the ensuing inflammatory response is quite similar consisting of a complicated set of functional and cellular adjustments involving changes in microcirculation, movement of fluids, and influx and activation of inflammatory cells (e.g. leukocytes). Examples of such diseases and conditions include: coronary artery disease, osteoporosis, nephropathy in diabetes mellitus, alopecia areata, Graves disease, systemic lupus erythematosus, lichen sclerosis, ulcerative colitis, diabetic retinopathy, periodontal disease, juvenile chronic arthritis (e.g. chronic iridocyclitis), psoriasis, insulin dependent diabetes in DR 3/4 patients, asthma, chronic inflammatory liver disease, chronic inflammatory lung disease, lung fibrosis, liver fibrosis, rheumatoid arthritis, ulcerative colitis and other acute and chronic inflammation diseases of the Central Nervous System (CNS), gastrointestinal system, the skin and associated structures, the immune system, the hepatobiliary system, or any site in the body where pathology can occur with an inflammatory component. As used herein, the term "inflammatory condition" further includes any disease with an IL-1 component, including rheumatoid arthritis, inflammatory bowel disorder, Type I diabetes, psoriasis, osteoporosis, nephropathy in diabetes mellitus, alopecia areata, Graves disease, systemic lupus erythematosus, lichen sclerosis, ulcerative colitis, coronary artery disease and other arteritic disorders, diabetic retinopathy, low birth weight and pregnancy complications, severe periodontal disease, psoriasis and insulin dependent diabetes.

The term "interact" as used herein is meant to include detectable relationships or association (e.g. biochemical interactions) between molecules, such as interaction between protein-protein, protein-nucleic acid, nucleic acid-nucleic acid, and protein-small molecule or nucleic acid-small molecule in nature.

The term "IL-1 related" as used herein is meant to include all mouse and human genes related to the human IL-1 locus genes on human chromosome 2 (2q 12–14). These include IL-1 genes of the human IL-1 gene cluster located at chromosome 2 (2q 13–14) which include: the IL-1A gene which encodes interleukin-1a, the IL-1B gene which encodes interleukin-1b, and the IL-1RN (or IL-1ra) gene which encodes the interleukin-1 receptor antagonist. Furthermore these IL-1 related genes include the type I and type II human IL-1 receptor genes located on human chromosome 2 (2q12) and their mouse homologs located on mouse chromosome 1 at position 19.5 cM. Interleukin-1a, interleukin-1b, and interleukin-1RN are related in so much as they all bind to IL-1 type I receptors, however only interleukin-1a and interleukin-1b are agonist ligands which activate IL-1 type I receptors, while interleukin-1RN is a naturally occurring antagonist ligand.

Where the term "IL-1" is used in reference to a gene product or polypeptide, it is meant to refer to all gene products encoded by the interleukin-1 locus on human chromosome 2 (2q 12–14) and their corresponding mouse homologs. The term IL-1 thus includes secreted polypeptides which promote an inflammatory response, such as IL-1a and IL-1b, as well as a secreted polypeptide which antagonizes inflammatory responses, such as IL-1 receptor antagonist and the IL-1 type II (decoy) receptor.

The term "IL-1 receptor" or "IL-1R" refers to various cell membrane bound protein receptors capable of binding to and/or transducing a signal from IL-1 locus-encoded ligand. The term applies to any of the proteins which are capable of binding interleukin-1 (IL-1) molecules and, in their native configuration as mammalian plasma membrane proteins, presumably play a role in transducing the signal provided by IL-1 to a cell. As used herein, the term includes analogs of native proteins with IL-1-binding or signal transducing activity. Examples include the human and murine IL-1 receptors described in U.S. Pat. No. 4,968,607. The term "IL-1 nucleic acid" refers to a nucleic acid encoding an IL-1 protein.

The term "IL-1 antagonist" as used herein is intended to include the genes and corresponding gene products of both the IL-1 receptor antagonist and the IL-1 type II (decoy) receptor.

The terms "IL-1 polypeptide" and "IL-1 protein" are intended to encompass polypeptides comprising the amino acid sequence encoded by the IL-1 genomic DNA sequences shown in FIGS. 1, 2, and 3, or fragments thereof, and homologs thereof and include agonist and antagonist polypeptides.

The term "IL-1 therapeutic" refers to various forms of IL-1 polypeptides, as well as peptidomimetics, nucleic acids, or small molecules, which can modulate at least one activity of an IL-1 polypeptide, e.g., interaction with an IL-1 receptor interaction, by mimicking or potentiating (agonizing) or inhibiting (antagonizing) the effects of a naturally-occurring IL-1 polypeptide. An IL-1 therapeutic which mimics or potentiates the activity of a wild-type IL-1 polypeptide is a "IL-1 agonist". Conversely, an IL-1 therapeutic which inhibits the activity of a wild-type IL-1 polypeptide is an "IL-1 antagonist".

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject IL-1 polypeptides preferably includes no more than 10 kilobases (kb) of nucleic acid sequence which naturally immediately flanks the IL-1 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "knock-out" refers to partial or complete suppression of the expression of an endogenous gene. This is generally accomplished by deleting a portion of the gene or by replacing a portion with a second sequence, but may also be caused by other modifications to the gene such as the introduction of stop codons, the mutation of critical amino acids, the removal of an intron junction, etc.

The term "knock-out construct" refers to a nucleic acid sequence that can be used to decrease or suppress expression of a protein encoded by endogenous DNA sequences in a cell. In a simple example, the knock-out construct is comprised of a gene, such as the IL-1RN gene, with a deletion in a critical portion of the gene so that active protein cannot be expressed therefrom. Alternatively, a number of termination codons can be added to the native gene to cause early termination of the protein or an intron junction can be inactivated. In a typical knock-out construct, some portion of the gene is replaced with a selectable marker (such as the neo gene) so that the gene can be represented as follows: IL-1RN 5'/neo/IL-1RN 3', where IL-1RN5' and IL-1RN 3', refer to genomic or cDNA sequences which are, respectively, upstream and downstream relative to a portion of the IL-1RN gene and where neo refers to a neomycin resistance gene. In another knock-out construct, a second selectable marker is added in a flanking position so that the gene can be represented as: IL-1RN/neo/IL-1RN/TK, where TK is a thymidine kinase gene which can be added to either the IL-1RN5' or the IL-1RN3' sequence of the preceding construct and which further can be selected against (i.e. is a negative selectable marker) in appropriate media. This two-marker construct allows the selection of homologous recombination events, which removes the flanking TK marker, from non-homologous recombination events which typically retain the TK sequences. The gene deletion and/or replacement can be from the exons, introns, especially intron junctions, and/or the regulatory regions such as promoters.

The term "knock-out mammal" and the like, refers to a transgenic mammal wherein a given gene has been suppressed by recombination with a knock-out construct. It is to be emphasized that the term is intended to include all progeny generations. Thus, the founder animal and all F1, F2, F3, and so on, progeny thereof are included.

The term "chimera," "mosaic," "chimeric mammal" and the like, refers to a transgenic mammal with a knock-out construct in some of its genome-containing cells.

The term "heterozygote" "heterozygotic mammal" and the like, refers to a transgenic mammal with a knock-out construct on one of a chromosome pair in all of its genome-containing cells.

The term "homozygote" "homozygotic mammal" and the like, refers to a transgenic mammal with a knock-out construct on both members of a chromosome pair in all of its genome-containing cells.

"Linkage disequilibrium" refers to co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. Alleles that co-occur at expected frequencies are said to be in "linkage equilibrium".

The term "marker" or "marker sequence" or similar phrase means any gene that produces a selectable genotype or preferably a selectable phenotype. It includes such examples as the neo gene, green fluorescent protein (GFP) gene, TK gene, β-galactosidase gene, etc. The marker sequence may be any sequence known to those skilled in the art that serves these purposes, although typically the marker sequence will be a sequence encoding a protein that confers a selectable trait, such as an antibiotic resistance gene, or an enzyme that can be detected and that is not typically found in the cell. The marker sequence may also include regulatory regions such as a promoter or enhancer that regulates the expression of that protein. However, it is also possible to transcribe the marker using endogenous regulatory sequences. In one embodiment of the present invention, the marker facilitates separation of transfected from untransfected cells by fluorescence activated cell sorting, for example by the use of a fluorescently labeled antibody or the expression of a fluorescent protein such as GFP. Other DNA sequences that facilitate expression of marker genes may also be incorporated into the DNA constructs of the present invention. These sequences include, but are not limited to transcription initiation and termination signals, translation signals, post-translational modification signals, intron splicing junctions, ribosome binding sites, and polyadenylation signals, to name a few. The marker sequence may also be used to append sequence to the target gene. For example, it may be used to add a stop codon to truncate IL-1RN translation.

The use of selectable markers is well known in the art and need not be detailed herein. The term "modulation" as used herein refers to both upregulation (i.e., activation or stimulation (e.g., by agonizing or potentiating)) and downregulation (i.e. inhibition or suppression (e.g., by antagonizing, decreasing or inhibiting)).

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous subject (for that gene), the mutation is said to be co-dominant.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant IL-1 genes is present and/or expressed or disrupted in some tissues but not others. The term "non-human mammal" refers to any members of the class Mammalia, except for humans.

As used herein, the term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs and as applicable to the embodiment being described, single (sense or antisense) and double-stranded polynucleotides.

The term "polymorphism" refers to the coexistence of more than one form of a gene or portion (e.g., allelic variant) thereof A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long.

A "polymorphic gene" refers to a gene having at least one polymorphic region.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA techniques, wherein generally, DNA encoding an IL-1 polypeptide is inserted into a suitable expression vector which is in turn used to transform a host cell to produce the heterologous protein. Moreover, the phrase "derived from", with respect to a recombinant IL-1 gene, is meant to include within the meaning of "recombinant protein" those proteins having an amino acid sequence of a native IL-1 polypeptide, or an amino acid sequence similar thereto which is generated by mutations including substitutions and deletions (including truncation) of a naturally occurring form of the polypeptide.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention to identify compounds that modulate an IL-1 bioactivity.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400 or 425 consecutive nucleotides of a vertebrate, preferably an IL-1 gene.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the IL-1 genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of IL-1 polypeptide.

As used herein, the term "transfection" means the introduction of a nucleic acid, e.g., via an expression vector, into a recipient cell by nucleic acid-mediated gene transfer. Methods for transformation which are known in the art include any electrical, magnetic, physical, biological or chemical means. As used herein, "transfection" includes such specific techniques as electroporation, magnetoporation, $Ca^{++}$ treatment, injection, bombardment, retroviral infection and lipofection, among others. "Transformation", as used herein, refers to a process in which a cell's genotype is changed as a result of the cellular uptake of exogenous DNA or RNA, and, for example, the transformed cell expresses a recombinant form of an IL-1 polypeptide or, in the case of anti-sense expression from the transferred gene, the expression of a naturally-occurring form of the IL-1 polypeptide is disrupted.

As used herein, the term "transgene" means a nucleic acid sequence (encoding, e.g., one of the IL-1 polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the IL-1 polypeptides, e.g. either agonistic or antagonistic forms. However, transgenic animals in which the recombinant IL-1 gene is silent are also contemplated, as for example, the FLP or CRE recombinase dependent constructs described below. Moreover, "transgenic animal" also includes those recombinant animals in which gene disruption of one or more IL-1 genes is caused by human intervention, including both recombination and antisense techniques.

The term "treating" as used herein is intended to encompass curing as well as ameliorating at least one symptom of the condition or disease.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

4.3 Target Interleukin-1 Antagonist Genes

The gene to be knocked out may be any gene involved in the interleukin pathway or cascade, provided that at least some sequence or mapping information on the DNA to be disrupted is available to use in the preparation of both the knock-out construct and the screening probes. We have exemplified the invention using the IL-1RN gene, but other genes from the IL-1 gene cluster can be targeted based on sequence and mapping information on the IL-1 gene cluster available at GenBank accession no. L32838 (Zahedi, et al, *Cytokine*, 6:1–9 (1994)). Clones can also be obtained using available sequence information and the methods well known in the art such as those described by Ausubel, et al (Eds), *Current Protocols in Molecular Biology* (1997, J. Wiley, NY).

In a preferred embodiment of the invention, the mouse IL-1RN gene on chromosome 2 at position 10.0 cM (www.informatics.jax.org/, accession MGI: 96547) is targeted for disruption. The genomic DNA sequene of the murine IL-1RN gene is shown in FIG. 1 (Matsushime et al. (1991) Blood 78: 616–23; and Shuck et al. (1991) Eur J. Irnmunol 21: 2775–80). The genes for human, mouse, and rat IL-1RN are similar to the genes for IL-1 alpha and IL-1 beta in intron-exon organization, indicating a likelihood of common evolutionary origin (Eisenberg et al. (1991) Proc Natl Acad Sci USA 88: 5232–6). This common intron-exon gene structure further facilitates the design of suitable species-specific target gene constructs. These target gene constructs include IL-1RN target gene knock-out and knock-in constructs which are specifically adapted to each of the various embodiments of the invention.

In another embodiment of the invention, the mouse IL-1 type II receptor gene on chromosome 1 at position 19.5 cM (www.informatics.jax.org/ accession MGI:96546) is targeted for disruption. The murine IL-1 type II receptor gene has been mapped by analysis of restriction fragment length polymorphisms in interspecific backcrosses to the centromeric end of chromosome 1, in a region that is syntenic to a portion of human chromosome 2. The murine Il-1rl gene has thus been separated from the IL-1 genes, which lie on murine chromosome 2 (Copeland (1991) Genomics 9: 44–50). The exon sequence of this gene is shown in FIG. 2 (McMahan et al. (1991) EMBO J 10: 2821–32). Target gene constructs include IL-1 type II receptor target gene knock-out and knock-in constructs which are specifically adapted to each of the various embodiments of the invention as described below.

4.4 Interleukin-1 Target Gene Constructs

In one embodiment, the clone to be used in producing the knock-out construct is digested with a restriction enzyme selected to cut at a location(s) such that a marker gene can be inserted at that location in the gene. In alternative embodiments, DNA sequences can be removed by partial digestion with a random nuclease at a single restriction enzyme cut in the gene.

The proper position for marker gene insertion is that which will serve to prevent expression of the native gene. This position will depend on various factors, including which sequences (exon, intron or promoter) are to be targeted (i.e., the precise location of insertion necessary to inhibit promoter function or to inhibit synthesis of the native exon) and the availability of convenient restriction sites within the sequence. In some cases, it is desirable to remove a large portion of the gene so as to keep the length of the knock-out construct comparable to the original genomic sequence when a marker gene is to be inserted into the knock-out construct.

In a preferred embodiment, nucleotides from the EcoRV site in exon 3 to the first XbaI site in exon 4 downstream of the translational stop codon are deleted.

The marker gene can be any nucleic acid sequence well known to those skilled in the art and that is detectable and/or assayable. Typically an antibiotic resistance gene is used or any other gene whose expression or presence in the genome can easily be detected. The marker gene is usually operably linked to a promoter from any source that will be active or can easily be activated in the cell into which it is inserted. However, the marker gene need not have its own promoter as it may be transcribed using the promoter of the targeted gene. In addition, the marker gene will normally have a polyA sequence attached to the 3' end of the gene for transcription termination of the gene. Preferred marker genes are aminoglycoside phosphotransferase gene (aph), the hygromycin B phosphotransferase gene, or any antibiotic resistance gene known to be useful as a marker in knock-out techniques.

The linear knock-out construct may be transfected directly into embryonic stem cells (discussed below), or it may first be placed into a suitable vector for amplification prior to insertion. Suitable vectors are known to those skilled in the art. Preferred vectors are those that yield reasonable amounts from *E. coli*. These include, but are not limited to, the pBluescript II SK vector (Stratagene, San Diego, Calif.) or pGEM7 (Promega Corp., Madison, Wis.). However, tt may be desirable to use a phage or cosmid vector where the construct is large.

4.5 Transgenic Animals

The invention further provides for transgenic animals, which can be used for a variety of purposes, e.g., to identify therapeutics agents for IL-1 mediated inflammatory disorders. Transgenic animals of the invention include non-human animals containing a heterologous IL-1 gene or fragment thereof under the control of an IL-1 promoter or under the control of a heterologous promoter. Accordingly, the transgenic animals of the invention can be animals expressing a transgene encoding a wild-type IL-1 protein or fragment thereof or variants thereof, including mutants and polymorphic variants thereof These animals can be used to determine the effect of expression of an IL-1 protein in a specific site or for identifying IL-1 therapeutics or confirming their activity in vivo.

The transgenic animals can also be animals containing a transgene, such as reporter gene, under the control of an IL-1 promoter or fragment thereof. These animals are useful, e.g., for identifying IL-1 drugs that modulate production of IL-1, such as by modulating IL-1 gene expression. An IL-1 gene promoter can be isolated, e.g., by screening of a genomic library with an IL-1 cDNA fragment and characterized according to methods known in the art. In a preferred embodiment of the present invention, the transgenic animal containing said IL-1 reporter gene is used to screen a class of bioactive molecules known as steroid hormones for their ability to modulate IL-1 expression. In a more preferred embodiment of the invention, the steroid hormones screened for IL-1 expression modulating activity belong to the group known as androgens. In a still more preferred embodiment of the invention, the steroid hormone is testosterone or a testosterone analog. Yet other non-human animals within the scope of the invention include those in which the expression of the endogenous IL-1 gene has been mutated or "knocked out". A "knock out" animal is one carrying a homozygous or heterozygous deletion of a particular gene or genes. These animals could be useful to determine whether the absence of IL-1 will result in a specific phenotype, in particular whether these mice have or are likely to develop a specific disease, such as high susceptibility to heart disease or cancer. Furthermore these animals are useful in screens for drugs which alleviate or attenuate the disease condition resulting from the mutation of the IL-1 gene as outlined below. These animals are also useful for determining the effect of a specific amino acid difference, or allelic variation, in an IL-1 gene. That is, the IL-1 knock out animals can be crossed with transgenic animals expressing, e.g., a mutated form or allelic variant of IL-1, thus resulting in an animal which expresses only the mutated protein and not the wild-type IL-1 protein. In a preferred embodiment of this aspect of the invention, a transgenic IL-1 knock-out mouse, carrying the mutated IL-1 locus on one or both of its chromosomes, is used as a model system for transgenic or drug treatment of the condition resulting from loss of IL-1 expression.

Methods for obtaining transgenic and knockout non-human animals are well known in the art. Knock out mice are generated by homologous integration of a "knock out" construct into a mouse embryonic stem cell chromosome which encodes the gene to be knocked out. In one embodiment, gene targeting, which is a method of using homologous recombination to modify an animal's genome, can be used to introduce changes into cultured embryonic stem cells. By targeting a IL-1 gene of interest in ES cells, these changes can be introduced into the germlines of animals to generate chimeras. The gene targeting procedure is accomplished by introducing into tissue culture cells a DNA targeting construct that includes a segment homologous to a target IL-1 locus, and which also includes an intended sequence modification to the IL-1 genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a IL-1 gene function through the use of a targeting transgene construct designed to undergo homologous recombination with one or more IL-1 genomic sequences. The targeting construct can be arranged so that, upon recombination with an element of a IL-1 gene, a positive selection marker is inserted into (or replaces) coding sequences of the gene. The inserted sequence functionally disrupts the IL-1 gene, while also providing a positive selection trait. Exemplary IL-1 targeting constructs are described in more detail below.

Generally, the embryonic stem cells (ES cells ) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) *J. Embryol. Exp. Mol. Biol.* 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934) Still another preferred ES cell line is the WW6 cell line (Ioffe et al. (1995) *PNAS* 92:7357–7361). The cells are cultured and prepared for knockout construct insertion using methods well known to the skilled artisan, such as those set forth by Robertson in: Teratocarcinomas and Embryonic Stem Cells: A Practical Approach, E.J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]).

A knock out construct refers to a uniquely configured fragment of nucleic acid which is introduced into a stem cell line and allowed to recombine with the genome at the chromosomal locus of the gene of interest to be mutated. Thus a given knock out construct is specific for a given gene to be targeted for disruption. Nonetheless, many common elements exist among these constructs and these elements are well known in the art. A typical knock out construct contains nucleic acid fragments of not less than about 0.5 kb nor more than about 10.0 kb from both the 5' and the 3' ends of the genomic locus which encodes the gene to be mutated. These two fragments are separated by an intervening fragment of nucleic acid which encodes a positive selectable marker, such as the neomycin resistance gene (neo$^R$). The resulting nucleic acid fragment, consisting of a nucleic acid from the extreme 5' end of the genomic locus linked to a nucleic acid encoding a positive selectable marker which is in turn linked to a nucleic acid from the extreme 3' end of the genomic locus of interest, omits most of the coding sequence for IL-1 or other gene of interest to be knocked out. When the resulting construct recombines homologously with the chromosome at this locus, it results in the loss of the omitted coding sequence, otherwise known as the structural gene, from the genomic locus. A stem cell in which such a rare homologous recombination event has taken place can be selected for by virtue of the stable integration into the genome of the nucleic acid of the gene encoding the positive selectable marker and subsequent selection for cells expressing this marker gene in the presence of an appropriate drug (neomycin in this example).

Variations on this basic technique also exist and are well known in the art. For example, a "knock-in" construct refers to the same basic arrangement of a nucleic acid encoding a 5' genomic locus fragment linked to nucleic acid encoding a positive selectable marker which in turn is linked to a nucleic acid encoding a 3' genomic locus fragment, but which differs in that none of the coding sequence is omitted and thus the 5' and the 3' genomic fragments used were initially contiguous before being disrupted by the introduction of the nucleic acid encoding the positive selectable marker gene. This "knock-in" type of construct is thus very useful for the construction of mutant transgenic animals when only a limited region of the genomic locus of the gene to be mutated, such as a single exon, is available for cloning and genetic manipulation. Alternatively, the "knock-in" construct can be used to specifically eliminate a single functional domain of the targetted gene, resulting in a transgenic animal which expresses a polypeptide of the targetted gene which is defective in one function, while retaining the function of other domains of the encoded polypeptide. This type of "knock-in" mutant frequently has the characteristic of a so-called "dominant negative" mutant because, especially in the case of proteins which homomultimerize, it can specifically block the action of (or "poison") the polypeptide product of the wild-type gene from which it was derived. In a variation of the knock-in technique, a marker gene is integrated at the genomic locus of interest such that expression of the marker gene comes under the control of the transcriptional regulatory elements of the targeted gene. A marker gene is one that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. For example, one such alternative marker is the green fluorescent protein (GFP). The GFP marker is particularly useful for the examination of gene expression in individual viable cells. Thus GFP and related markers are particularly useful for in situ analysis of levels of expression of the "knocked-in" gene. All such markers are contemplated as being included within the scope of the teaching of this invention.

As mentioned above, the homologous recombination of the above described "knock out" and "knock in" constructs is very rare and frequently such a construct inserts nonhomologously into a random region of the genome where it has no effect on the gene which has been targeted for deletion, and where it can potentially recombine so as to disrupt another gene which was otherwise not intended to be altered. Such nonhomologous recombination events can be selected against by modifying the abovementioned knock out and knock in constructs so that they are flanked by negative selectable markers at either end (particularly through the use of two allelic variants of the thymidine kinase gene, the polypeptide product of which can be selected against in expressing cell lines in an appropriate tissue culture medium well known in the art—i.e. one containing a drug such as 5-bromodeoxyuridine). Thus a preferred embodiment of such a knock out or knock in construct of the invention consist of a nucleic acid encoding a negative selectable marker linked to a nucleic acid encoding a 5' end of a genomic locus linked to a nucleic acid of a positive selectable marker which in turn is linked to a nucleic acid encoding a 3' end of the same genomic locus which in turn is linked to a second nucleic acid encoding a negative selectable marker Nonhomologous recombination between the resulting knock out construct and the genome will usually result in the stable integration of one or both of these negative selectable marker genes and hence cells which have undergone nonhomologous recombination can be selected against by growth in the appropriate selective media (e.g. media containing a drug such as 5-bromodeoxyuridine for example). Simultaneous selection for the positive selectable marker and against the negative selectable marker will result in a vast enrichment for clones in which the knock out construct has recombined homologously at the locus of the gene intended to be mutated. The presence of the predicted chromosomal alteration at the targeted gene locus in the resulting knock out stem cell line can be confirmed by means of Southern blot analytical techniques which are well known to those familiar in the art. Alternatively, PCR can be used.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. For example, if the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knock out construct as explained above. Where more than one construct is to be introduced into the ES cell, each knockout construct can be introduced simultaneously or one at a time.

After suitable ES cells containing the knockout construct in the proper location have been identified by the selection techniques outlined above, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, the transformed ES cells can be microinjected into blastocytes. The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the IL-1 gene knocked out in various tissues of the offspring by probing the Western blot with an antibody against the particular IL-1 protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a IL-1-gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

A IL-1 transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a IL-1 protein can be essential for many forms of lineage analysis and can additionally provide a means to assess the effects of, for example, lack of IL-1 expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques, which allow for the expression of transgenes can be regulated via site-specific genetic manipulation in vivo, are known to those skilled in the art. For instance, genetic systems are available which allow for the regulated expression of a recombinase that catalyzes the genetic recombination of a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject IL-1 proteins. For example, excision of a target sequence which interferes with the expression of a recombinant IL-1 gene, such as one which encodes an antagonistic homolog or an antisense transcript, can be designed to activate expression of that gene. This interference with expression of the protein can result from a variety of mechanisms, such as spatial separation of the IL-1 gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the crelloxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant IL-1 protein can be regulated via control of recombinase expression.

Use of the cre/loxP recombinase system to regulate expression of a recombinant IL-1 protein requires the construction of a transgenic animal containing transgenes encoding both the Cre recombinase and the subject protein. Animals containing both the Cre recombinase and a recombinant IL-1 gene can be provided through the construction of "double" transgenic animals. A convenient method for providing such animals is to mate two transgenic animals each containing a transgene, e.g., a IL-1 gene and recombinase gene.

One advantage derived from initially constructing transgenic animals containing a IL-1 transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic IL-1 transgene is silent will allow the study of progeny from that founder in which disruption of IL-1 mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the IL-1 transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a IL-1A transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with H-$2^b$, H-$2^d$ or H-2q haplotypes such as C57BL/6 or DBA/1. The line(s) used to practice this invention may themselves be transgenics, and/or may be knock-outs (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1-2pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required;

however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a IL-1 protein (either agonistic or antagonistic), and antisense transcript, or a IL-1 mutant. Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1 98 1) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

4.6 Pharmaceutical Screens

4.6.1 General

The invention provides various transgenic cell lines and organisms in which pharmaceutical screens can be conducted to identify compounds capable of inhibiting IL-1 mediated inflammatory processes. As set forth above, the transgenic cell lines and organisms are engineered to be deficient in one or more endogenous IL-1 antagonizing gene activities. The resultant increase in endogenous IL-1 agonist activity (e.g. IL-1 alpha and IL-1 beta) generally leads to an "acute phase response." The acute phase response initiates further inflammatory processes, including those distinctive of the various inflammatory diseases and conditions discussed above. The acute phase response is characterized by the production of various acute phase markers, including the serum proteins SAP (in mice) and CRP (in humans). The seminal significance of the acute phase response in initiating these various inflammatory disease processes allows the use of such acute phase markers in the assessment of candidate drug compounds which are able to antagonize IL-1 mediated inflammatory disease processes.

4.6.2 Acute Phase Response

The acute phase response is triggered by cytokines produced by activated mononuclear phagocytes, lymphocytes, and other differentiated cell types in response to an inflammatory stimulus. Cytokines act locally and systemically to recruit and activate target cells including some that produce additional cytokines. This results in a cascade of events controlled and coordinated principally by the various cytokines elicited. The ensuing activation and pro-liferation of target cells and tissues, with the consequent alteration in cellular phenotype, enhances host survival by neutralizing the inflammatory agent, and by promoting repair processes and a return to homeostasis. This section focuses on our current understanding of the local and systemic effects of inflammatory cytokines including interleukin-1 (IL-1).

Interleukin-1 is generally regarded as the pro-inflammatory cytokine that is of central importance in the initiation and maintenance of the acute phase response. Originally named 'endogenous pyrogen' for its ability to induce fever, IL-1 has, over the past 20 years, had other acronyms based on its multiple biological activities. These include lymphocyte activating factor, thymocyte proliferation factor, and helper peak-1 for its ability to induce thymocyte activation and proliferation; B cell activating factor for its ability to stimulate direct activation of plasma cells; leucocyte endogenous mediator for its ability to induce acute phase protein synthesis; and mononuclear cell factor, monocute derived recruiting activity, catabolin, osteoclast-activating factor, and haemopoietin-I which reflect its role in a wide range of additional physiological processes. All of the above functions were eventually attributed to a 17.5 kDa protein which was given the inclusive name of interleukin-1 (Aarden, et al. (1979) J Immunol, 123: 2928–9). There are two isoforms of human IL-1: IL-Iα of pI 5.0 and IL-Iβ of pI 7.0. Both isoforms have been cloned and sequenced establishing that both molecules are synthesized as pro-peptides of approximately 31 kDa that are processed to the mature 17.5 kDa products. The generation of the mature IL-1β molecule from its pro-peptide requires a proteolytic cleavage event that is mediated by a specific, apparently unique enzyme, the interleukin-1β converting enzyme, which has recently been defined at the molecular level. The existence of such an enzyme implies a precise control mechanism governing the production of the active form of this cytokine, and indicates the likelihood that the production of this, and other active inflammatory mediators, is subject to specific and finely tuned control pathways.

Although IL-1 is considered primarily a product of activated mononuclear phagocytes, given the proper stimulatory signal it is synthesized by a number of other differentiated cell types, including lymphocytes (helper T cells, B cells, NK cells, neutrophils, and large granular lymphocytes); vascular cells (smooth muscle and endothelial cells); epithelial cells of the cornea and thymus; skin cells (keratinocytes, Langerhans cells); brain cells (astrocytes, microglial cells, glioma cells); dendritic cells; mesangial cells of the kidney; fibroblasts; and chondrocytes. Mononuclear phagocytes can be stimulated to produce IL-1 in response to a number of activating stimuli such as contact with T cells (during antigen presentation), viruses, bacteria, antigen-antibody complexes, and some chemicals.

IL-1 also acts directly on the central nervous system (CNS) by stimulating the hypothalamus and by synergizing with prostaglandins, thereby modulating the firing rate of thermoregulatory neurons in the brain and causing fever. This brings about the production of corticotrophin releasing factor (CRF) and adrenocorticotrophic hormone (ACTH) which results in glucocorticosteroid synthesis. The induction of elevated levels of glucocorticosteroids by IL-1 in turn creates a negative feedback regulatory loop, since IL-1 synthesis in activated macrophages is inhibited by glucocorticosteroids. The initiation of the above cascade and its pro-inflammatory sequelae therefore sets the program which, if uninterrupted, leads to a return to homeostasis. Significantly, another activity of interleukin-1 in the brain is a stimulation of the beta-amyloid precursor promoter (Donnelly et al. (1990) Cell Mol Neurobiol, 10: 485–95), suggesting an association between Alzheimer's disease and IL-1 mediated inflammatory processes.

A return to homeostasis is probably also promoted by the induction, possibly by IL-1 itself, of the interleukin-I receptor antagonist protein (IL-1RN/IL-1 ra/IRAP). IL-1RN inhibits IL-1 agonist activity by binding to the IL-1 receptors on target cells thereby directly blocking the engagement of IL-1 and the consequent transduction of signals via the receptors (Hannum et al. (1990) Nature 343: 336–41). IL-1RN is synthesized at increased levels in the livers of mice undergoing experimentally induced inflammation at a time when the hepatic synthesis of acute phase reactants is at its maximum (Zahedi, et al. (1991) J. Immunol, 146: 4228–33). The induction of the antagonist therefore coincides with the peak of the systemic acute phase response when the pro-inflammatory role of IL-1 (and other cytokines) has been fulfilled.

During the acute phase response, IL-1 triggers cell-mediated, humoral, and natural immune responses by acting on T cells, B cells, or NK cells directly, or by stimulating these target cells indirectly by inducing the synthesis of other cytokines that can provide them with additional positive or negative regulatory signals. IL-1 is also important for B cell maturation and antibody production. Circulating IL-1 coordinates cellular mobilization by accelerating the release of mature neutrophils from the bone marrow into the bloodstream, and by acting as a chemoattractant, drawing neutrophls, T cells, and monocytes to sites of inflammation. At the site of inflammation, IL-1 induces proliferation of fibroblasts and epithelial cells and enhances the adherence of lymphocytes to sites of tissue damage by inducing the synthesis of the intercellular adhesion molecule-1 (ICAM-1) on endothelial cells and epithelial cells. IL-1 promotes wound hearing by stimulating the synthesis of the clotting factors plasminogen activator and its inhibitor, procoagulant, platelet activating factor, collagens, and collagenase.

In short IL-1 generally behaves as a multi-functional hormone by signalling a variety of cells to make more IL-1 and/or other cytokines; by stimulating the CNS; by inducing hepatic APR synthesis; and by coordinating local cell signalling at the site of inflammation.

Cytokines modulate gene expression in target tissues by first binding to specific receptors on the target cell surface. The ligand-receptor complex then provides a signal that is transduced from the inner face of the plasma membrane to the nucleus. The mechanism by which this signal is transduced may be specific to the target cell.

There are two distinct membrane receptors for IL-1 (Chizzonite, et al. (1989) Proc Nat Acad Sci USA 86: 8029–33): an 80 kDa (type 1) receptor present on T cells, fibroblasts, and connective tissue cells, and a 67 kDa (type 2) receptor, found only on B cells. Both receptors have an extracellular domain, a short transmembrane domain, and a cytoplasmic domain. Both bind IL-1α and IL-1β; however, only the 80 kDa receptor is capable of interaction with the IL-1 receptor antagonist protein (IL-1RN) (Hannum et al. (1990) Nature 343: 336–41).

Cytokines modulate cellular activities by activating protein kinases via at least two major pathways. One pathway involves the conversion of ATP to cAMP, a second messenger that is generated by membrane adenylate cyclase. The other mechanism involves the hydrolysis of the membrane lipid pliosphatidylinositol-4,5-triphosphate by phospholipase C, which yields diacylglycerol (DAG) and inositol-1,4,5-triphosphate (IP3). Phosphoinositide hydrolysis results in DAG binding to protein kinase C. Activated cAMP and DAG are capable of modifying the activity of protein kinases A and C respectively. With regard to IL-1 signal transduction, some investigators report the involvement of cAMP or DAG as second messengers while others dispute the involvement of either. This controversy is extended to whether or not activation of IL-1 responsive genes occurs via different signalling pathways in different cell types. Recent evidence suggests that the signal transduction pathway leading to the activation of IL-1 responsive genes in fibroblasts and connective tissue cells involves phosphorylation events mediated by serine kinases (see Kanakaraj, et al. (1998) J Exp Med 15: 2073–9).

Many receptor-ligand complexes are coupled to guanosine nucleotide binding proteins (G proteins, e.g. Gs, Gi, Go, Gt) which bind GTP and transduce signals from the occupied receptors to effector enzymes such as adenylate cyclase, phospholipase C or phospholipase A2. G proteins have been implicated in mediating the generation of DAG by the modulation of phospholipase C activity. Activation of G proteins is accompanied by enhanced GTP binding and GTPase activity, and their roles in IL-1 signal transduction can be analysed experimentally using radiolabelled GTP analogues or measuring GTP hydrolysis in IL-1 treated cells or membrane preparations. For most receptor-ligand complexes, pretreatment of cells with pertussis toxin (IAP) causes G proteins to uncouple. This is due, in the case of 'classical' G proteins, to ribosylation of ADP by the A subunit of the toxin. IL-1α and IL-1β cause increased GTPase activity and activation of G proteins in membranes prepared from thymoma cells due to an increased affinity for GTP (64). Pretreatment of thymomas and B cells with intact pertussis toxin partially inhibits the IL-1 induced G protein activity. However, the B subunit of the toxin, which does not contain ADP ribosylating activity, inhibits G protein activation as efficiently as the intact pertussis toxin. Inhibition of G protein activation by IL-1 is therefore not attributable to ADP ribosylation. It appears, therefore, that pertussis toxin inhibition of IL-1 signal transduction does not involve inactivation of a classical G protein, but may be due to the inactivation of some other 'G-like' protein. Such non-classical pertussis-sensitive G protein activation has been demonstrated for IL-2, TNF, and GM-CSF signaling mechanisms.

Although the early signals required for IL-1 signal transduction remain under debate, the increased transcription of APR RNAs consequent to IL-I receptor interactions requires the activation of factors that bind to the 5' regulatory regions of the IL-1 responsive genes. The activation of the cytoplasmic transcription factor nuclear factor kappa B (NFκB) is via the IL-1-induced phosphorylation and dissociation of its associated inhibitor protein IκB thereby allowing it to enter the nucleus and bind to DNA. NFκB is centrally involved in the IL-1 directed gene activation of a number of APR genes. Thus IL-1 signaling involves the mobilization of preexisting transcription factors. In addition, the induction of gene expression in IL-1 responsive genes can be achieved with phorbol myristate acetate (PMA) which activates the transcription factors c-fos/c-jun that bind to AP1 sites in the promoters. As both PMA and IL-1 can stimulate the synthesis of these DNA binding proteins the capacity of IL-1 to increase the absolute levels of transcription factors represents an additional means of control of gene expression.

One of the most dramatic consequences of the acute phase response is the radically altered biosynthetic profile of the liver. Under normal conditions the liver synthesizes a characteristic range of plasma proteins at steady state concentrations. Many of these proteins have important functions that are required during the acute phase response and consequently are induced following an inflammatory stimulus. Conversely others, in particular albumin, are down-regulated to allow an increase in the capacity of the liver to synthesize the induced 'acute phase reactants' (APRs). APRs have a wide range of activities that contribute to host defense: they stimulate and participate in immune responses; sequester essential co-factors and cell types, and direct them to sites of tissue damage; directly neutralize inflammatory agents, and help to minimize the extent of tissue damage locally; and participate in tissue repair and regeneration.

Proteins that participate in the complement, coagulation, and contact (kinin-forming) cascades that increase in plasma concentration during the acute phase enhance the host's ability to destroy invading micro-organisms and provide essential blood clotting components. The induced complement components include C2, C3, C4, C5, C9, C4 binding protein (C4bp), and factor B. In addition to their cytolytic activity, complement proteins have a wide range of activities in natural immunity. Activation of the complement cascade ultimately results in the local accumulation of neutrophils, macrophages, and plasma proteins that participate in the killing of infectious agents, the clearance of foreign and host cellular debris, and the repair of damaged tissue. Plasma levels of fibrinogen, the precursor to the clot-forming protein fibrin, are increased during the acute phase response (Mossesson and Doolittle (1983) Ann NY Acad Sci, 408: 1–672) to provide an ample supply of one of the critical proteins involved in limiting local tissue damage and the entry of pathogens, and in promoting wound healing. Fibrinogen levels have, in addition, been useful clinically in determining the 'erythrocyte sedimentation rate', an important indicator of inflammation as the absolute concentration of fibrinogen correlates with the rate at which erythrocytes sediment.

A number of proteinase inhibitors are APRS, including α1-antitrypsin, α1-antichymotrypsin, α2-antiplasmin, C1 inhibitor, and inter-α-trypsin inhibitor. These inhibitors help to neutralize the lysosomal hydrolases released following the infiltration and activation of macrophages and neutrophils. Thus inappropriate collateral damage to healthy host tissues is kept to a minimum.

The plasma levels of metal transport proteins such as haptoglobin, haemopexin, and caeruloplasmin are increased during the acute phase response. Haptoglobin and haemopexin bind haemoglobin and the haem moiety, respectively, and prevent iron loss during infection and injury. In addition they minimize the levels of haem iron available for uptake by bacteria thereby depriving the infectious agent of an essential nutrient and further increasing the host's resistance to infection. Caeruloplasmin is involved in copper and iron transport and acts as a scavenger for the removal of oxygen-free radicals released by macrophages and neutrophils which can cause further tissue damage.

The plasma proteins albumin, pre-albumin, transferrin, apolipoprotein AI, and apolipoprotein AII are decreased during the acute phase response and are therefore termed 'negative APRs'.

A subset of APRs are massively induced. Serum amyloid A protein (SAA) and one of the pentraxins, either C-reactive protein (CRP) or serum amyloid P component (SAP) depending on species, are increased by up to a thousandfold during inflammation. These 'major' APRs are considered in more detail later.

The changes in the plasma concentrations of individual APRs are variable, and probably reflect differences in the amount of each protein that is required to participate effectively in the acute phase response. The magnitude of increase (or decrease) in APR plasma concentration varies (Table 1) from only 50 per cent (caeruloplasmin, C3), to a moderate 2–4-fold (proteinase inhibitors, haptoglobin, fibrinogen), to over 1000-fold (CRP, SAA) (reviewed in Kushner et al. (1982) Ann NY Acad Sci, 389: 235–74). The kinetics of human APR induction are characterized by increased plasma levels of CRP, SAA, and α1-antichymotrypsin within the first 12 hours after the acute stimulus, followed by α1-antitrypsin, α1-acid glycoprotein, haptoglobin, and factor B levels increasing approximately 24 hours later. CRP and SAA proteins have very short half-lives (5–7 hours), whereas most APRs have half-lives of 3–5 days (reviewed in Laurent (1989) Acute phase proteins in the acute phase response (Springer-Verlag) pp. 150–160). After the acute phase response, plasma concentrations of APRs return to their normal values; some APRs, however, remain elevated indefinitely in the case of chronic inflammation. Patterns of the acute phase response in various infectious diseases and inflammatory conditions have been extensively reviewed by others.

APR induction profiles differ greatly between species, although APRs in different species share a high degree of structural and functional homology. For example, CRP but not SAP is a major APR in humans; conversely, in mice (undergoing experimentally induced inflammation) SAP is a major APR whereas CRP is only a minor APR (reviewed in Pepys and Baltz (1983) Adv Immunol 34: 141–212). Humans, mice, and rabbits exhibit a dramatic induction of SAA during the acute phase response but rats do not. Moreover, the proteinase inhibitor α2-macroglobulin does not increase in plasma concentration in humans during the acute phase response but in mice and rats it is a significantly induced APR (Lonberg-Hom et al. (1987) J Biol Chem 262: 438–45).

A summary of the available acute phase response markers available for monitoring the effectiveness of candidate drug compounds in inhibiting IL-1 mediated inflammation is provided below in Table 1. Preferred acute phase markers are those which show the greatest enhancement in expression following IL-1 induction.

TABLE 1

Acute phase reactants and relative change in plasma concentration during the acute phase response.

| Acute phase reactant | Fold change |
|---|---|
| Complement and clotting components | |
| C2 | + |
| C3 | + |
| C4 | ++ |
| C4 binding protein (C4bp) | ++ |
| C9 | ++ |
| Factor B (FB) | +++ |
| Fibrinogen (FGN) | +++ |
| Proteinase inhibitors | |
| α2-Antiplasmin (a2AP) | ++ |
| α1-Mtitrypsin (a1AT) | +++ |
| α1-Antichymotrypsin (a1ACT) | +++ |
| C1 Inhibitor (Clinh) | +++ |
| inter-α-trypsin inhibitor (IαTinh) | + |
| Metal transport proteins | |
| Caeruloplasmin (CER) | ++ |
| Haptoglobin (HP) | +++ |
| Haemopexin (HXN) | ++ |
| Major APRs | |
| α1-Acid glycoprotein (α1AGP) | +++ |
| C-Reactive protein (CRP) | ++++ |
| Serum amyloid A (SAA) | ++++ |
| Negative APRs | |
| Albumin (Alb) | − |
| Apolipoprotein AI (ApoAI) | − |
| Apolipoprotein AII (ApoAII) | − |
| Transferrin (TFN) | − |

+, <1.5-fold increase; ++, 1.5–2-fold increase;
+++, 2–5-fold increase; ++++, >1 000-fold increase;
−, 1.5–2-fold decrease.

The kinetics and magnitude of APR biosynthesis in response to in vivo inflammatory stimuli is based largely on studies using rodent models. In the early studies, rabbits and mice were injected with bacterial lipopolysaccharide (LPS) or an inflammatory chemical stimulus such as turpentine, azocaesein, or thioglycollate, and plasma and tissue levels of APR protein and mRNA were determined. Purified and recombinant cytokines became available thereafter and allowed the effects of individual cytokines on the acute phase response in general, and APR synthesis in particular to be analysed in vivo. However, these studies are complicated by additional inflammatory processes elicited by cytokines which produce a spectrum of responses (as detailed earlier) that are secondary or consequent to the direct effect of the agent under test. Primary hepatocyte cultures been used by a number of investigators; however, it is also often difficult to differentiate between primary and secondary effects in these studies as liver cell cultures can contain a number of other cell types such as fibroblasts and Kupffer cells which may become stimulated by test cytokines to produce additional factors that can synergize with or inhibit the mediator being analysed. Cultured hepatoma cell lines such as PLC/PRF/5, HepG2, Hep3B, and HuH-7 provide useful models for the study of individual APR genes by inflammatory mediators under culture conditions. However the APRs expressed by these cell lines can respond very differently to cytokine treatments in terms of their capacity to be induced and their magnitude of induction, and in some instances different investigators have reported conflicting results using the same cell line. Human hepatoma/hepatocyte cultures nevertheless do constitute useful models for the study of common mechanisms by w defined cytokines, alone or in combinations, modulate human APR gene expression.

The differential response of individual APRs to different inflammatory mediators is summarized in Table 2 (reviewed in Gauldie (1989) Acute phase proteins in the acute phase response. pp. 1–22 Springer-Verlag). IL-1, IL-6, and TNF are each capable of inducing the biosynthesis of a number of human APRs, (e.g. α1-antichymotrypsin, α1-acid glycoprotein, caeruloplasmin, C3, factor B, SAA) and causing a decrease in the biosynthesis of others, (e.g. alpha fetoprotein). IL-1, but not IL-6 or TNF, also decreases the synthesis of C1 inhibitor and SAP in human hepatoma cells. With respect to the synthesis of other APRs the responses of hepatoma cells to each of these cytokines is heterogeneous: for some APRS, biosynthesis is induced only by IL-6 and not by IL-1, (e.g. C4bp, SAP, haemopexin, haptoglobin, fibrinogen). Co-treatment of cells with IL-1 plus IL-6 has an additive or synergistic effect on some APR genes (α-acid glycoprotein, CRP, C3, factor B, haptoglobin, SAA). Alternatively one cytokine can exert an inhibitory effect which overrides the action of an inducing cytokine; for example IL-1 and TNF can inhibit the up-regulation by IL-6 of C1 inhibitor and SAP synthesis, and of CRP, haptoglobin, fibrinogen, and SAA synthesis, respectively.

TABLE 2

The regulation of various acute phase reactants by different cytokines

| | IL-1 | IL-6 | TNFA | TGFβ | IFNγ |
|---|---|---|---|---|---|
| α1ACT | + | + | + | + | -- |
| α1AGP | + | + | + | | |
| α1AT | | + | + | | + |
| αFP | | -- | | | - |
| Alb | -- | | | | - |
| ApoAI | | | | | - |
| ApoAII | | | | | - |
| Clinh | -- | + | | | |
| C2 | + | | | | + |
| C3 | + | + | + | | |
| C4 | | | | | + |
| C4bp | | + | + | | |
| CER | + | + | + | | |
| CRP | | + | | | |
| FB | + | + | + | | + |
| FGN | | + | -- | -- | |
| FN | -- | -- | | | + |
| H P | + | + | + | | -- |
| HXN | | + | | | |
| 1αtinh | + | | | | |
| SAA | + | + | + | | + |
| SAP | -- | + | | | |
| TFN | | -- | -- | | |

+, up-regulation; --, down regulation. No symbol is either no change or not tested. See Table 1 for abbreviations.

The glucocorticosteroid dexamethasone greatly enhances the response of some APRs to cytokines in cell culture systems (80), though it is generally unable to induce APR synthesis on its own. This emphasizes an important feature of the acute phase response: as discussed earlier, IL-1 stimulates the CNS to produce glucocorticosteroids that enhance the capacity of IL-1 to induce APR synthesis in the liver while at the same time down-regulating further IL-1 synthesis by activated monocytes. Dexamethasone, a synthetic glucocorticosteroid, is therefore often routinely included at approximately physiological concentrations in the experimental cytokine treatment protocols o augment their inductive effects.

IFNγ has more limited effects than IL-1, IL-6, and TNF on APR synthesis. Most studies of IFNγ APR induction have used mouse L cells transfected with the APR gene of interest. In these studies the biosynthesis of SAA, C2 and factor B, and C4 can be induced. IFNY also induces the synthesis of human factor B and C2 genes in primary monocytes. It has been suggested that IFNγ alters hepatocyte responsiveness indirectly by modulating the number of cellular cytokine receptors. TGFβ has also recently been shown to regulate the synthesis of a number of APRs.

Serum amyloid A protein (SAA), C-reactive protein (CRP), and serum amyloid P component (SAP) can be induced to up to a thousand-fold of their normal plasma concentrations (reviewed in Kushner, et al. (1982) Ann NY Acad Sci 389: 235–74) during the acute phase, and therefore constitute a distinct subgroup of APRS. They are often referred to as 'major' acute phase proteins. Studies of SAA, CRP, and SAP illustrate many of the challenges posed by research into the organization, structure, function, and control of expression of APRS. The extreme alterations in the biosynthesis of these major APRs indicate that they are of considerable biological interest. Although their precise physiological roles remain undefined and are the subject of considerable debate the magnitude and rapidity of their induction following an acute phase stimulus, together with their short half-lives (around six hours, whereas those of other APRs are measured in days), suggest that there is a particular requirement for these proteins very early in the establishment of host defense. They are therefore likely to be of considerable clinical importance and are likely to have a critical protective role.

CRP and SAP are pentraxins, proteins with a characteristic pentameric con-figuration of five subunits arranged as a disc. Generally only one pentraxin is a major APR in a given species, the other being expressed essentially constitutively. In man (Kushner, et al. (1978) J Clin Invest 61: 235–42) and rabbit CRP is the inducible pentraxin whereas in the mouse it is SAP (Pepys et al. (1979) Nature 278: 259–61). The apparent paradox of the species-specific alternate expression of pentraxins is unresolved though it is likely that the requirement for an acute phase pentraxin during inflammation is met by some common physiological activity invested in the particular molecule induced. Such a common function has not yet been defined.

CRP was originally named for its ability to bind the C-polysaccharide of pneumococcus. Subsequently it has been shown to function in vitro as an opsonin for bacteria, parasites, and immune complexes; in addition it can initiate the complement cascade and enhance macrophage tumouricidal activity. The exquisite responsiveness of CRP to an acute phase stimulus and its wide concentration range, together with ease of measurement have led to CRP plasma levels being used to monitor accurately the severity of inflammation and the efficacy of disease management.

SAP was originally named because it is found in serum and is the circulating form of the amyloid P (AP) component (90). AP is one of the two major constituents of the amyloid deposits which are the occasional consequence of a range of chronic recurrent inflammatory diseases It is a normal component of basement membranes and has the capacity to bind to fibronectin. Unlike CRP, it has no obvious immune-related function.

CRP and SAP display about 50 per cent amino acid identity confirming the relatedness implied by their gross structural similarities. The genes encoding CRP and SAP have remained in close physical and genetic linkage in man and mouse. They map to syntenic regions in both species: band q2.1 of chromosome 1 and the distal portion of chromosome 1 in man and mouse respectively. Flanking loci in both species include many genes with immune and inflammation related roles: all of the Fc receptors to date have been mapped to the same regions as have a group of interferon inducible products in mouse. It is likely therefore that the entire region around the pentraxin genes will be of considerable scientific and clinical importance and fine mapping studies are being undertaken in the authors' and other laboratories. CRP and SAP from a number of mammalian species have been cloned and sequenced. Computer based evolutionary analyses have revealed that their genes probably duplicated from a common ancestral pentraxin gene early in mammalian evolution (approximately 200 million years ago, prior to the time of the divergence of eutherian mammals and marsupials). The proteins are evolving at twice the rate of most other products of gene duplication in mammals. Future studies to identify the putative pentraxin activity that is essential in conferring a protective function during the acute phase response should therefore be directed towards the regions of the molecules that have retained much higher levels of similarity than those displayed by CRP and SAP as a whole. One candidate activity is suggested by the capacity of both pentraxins to bind to chromatin. The ability to bind to and effect the clearance of nuclear material released from necrotic tissue during inflammation would provide an efficient means of precluding the initiation of auto-immune processes directed towards nuclear antigens and would explain, at least in part, the required presence of high circulating levels of pentraxins during inflammation.

The acute phase expression of CRP and SAP has been extensively studied in vivo and in vitro. In a recent study, mice given a single experimental acute phase stimulus, for example via intraperitoneal injection of thioglycollate or subcutaneous injection of azocaesein, show massive increases in hepatic SAP mRNA levels within 2–4 hours and peak concentrations by 8–12 hours. These are superseded by dramatically elevated circulating SAP protein levels peaking around 24–36 hours. Background levels of both hepatic mRNA and plasma protein are re-established by 72 hours in accord with the transient nature of the acute phase response. The magnitude and kinetics of SAP mRNA and protein induction is stimulus-specific, indicating that the cytokine cascade and the counterbalancing controls that modify, reduce, and terminate the consequent pro-inflammatory signalling are themselves subject to exquisite control and do not merely follow a pre-set programme.

In vitro studies using human hepatoma cultures treated with inflammatory mediators such as monocyte conditioned medium and recombinant IL-1β and recombinant IL-6 have revealed some of the intrinsic genetic elements and biosynthetic controls which are important in determining the level of pentraxin expression. In such studies CRP mRNA and protein synthesis is induced by IL-6. Although no significant change is elicited by IL-1β alone, in combination with IL-6 there is a massively enhanced response compared with that to IL-6 alone. The location of the IL-6 response elements have been fine mapped in the CRP promoter. SAP mRNA can be induced in human PLC/PRF/5 cells by treatment with recombinant IL-6; treatment with recombinant IL-1β down-regulates SAP mRNA synthesis, an effect which predominates when both cytokines are present. This suggests that, although human SAP is not considered to be a significant acute phase protein, there may be conditions, especially at local sites, under which the relative cytokine proportions present would promote increased non-hepatic SAP synthesis. The above in vitro results show that the cytokine-specific responses of related liver products differ during the acute phase response. That the differential responses of the same liver protein between species are generally dependent upon intrinsic genetic control elements is illustrated by the capacity of mice, in which CRP is a very minor APR, to induce greatly a human CRP transgene using the endogenous mouse cytokine, signal transduction, and cellular biosynthetic pathways.

SAA is a major acute phase protein in most mammalian species, and is the most dramatically induced. The kinetics of its induction by different inflammatory stimuli in mouse in vivo studies parallel those discussed above for SAP. SAA is a small apolipoprotein (104 amino acids in human) which, during the acute phase response, associates with high density lipoprotein (HDL) , in particular HDL3. SAA can become the predominant apolipoprotein associated with HDL3, exceeding apolipoprotein AI. SAA is the product of multiple related genes in several species. These genes have a common organization, four exons and three introns, which is reminiscent of several other apolipoprotein genes. In humans two acute phase SAA (A-SAA) genes have been described: SAA I and SAA2 are almost identical with respect to the primary structures of their specified products, their gene organizations and sequences, and their mode of expression. They are undoubtedly the result of an ancestral gene duplication followed by regular gene conversion events. In addition there is a third gene (SAA3) for which no MRNA or protein product has been described. Although it was originally reported to have the structural integrity of an authentic transcribed gene, the presence of an in-frame stop codon was subsequently identified indicating that it is in fact a pseudogene. Recently, we have identified the product of a fourth SAA gene: C-SAA ('constitutive' SAA) is present on normal HDL3 and is minimally induced, if at all, during acute inflammation. Its expression is therefore radically different from that of the A-SAAS. Sequence analysis of a C-SAA cDNA clone predicts a mature molecule of 112 amino acids with only 55 per cent identity to the SAA1 and SAA2 proteins. The extra 8 amino acids present in C-SAA reside in an octapeptide that is positioned relative to the A-SAA sequence between residues 69 and 70. Although, based on sequence identity and content, and on induction capacity, C-SAA is a more distantly related member of the SAA superfamily than the A-SAA genes SAA1 and SAA2, it is nevertheless closely linked to these genes. We have mapped the C-SAA gene to the SAA4 locus located 9 kb downstream from the SAA2 locus. In addition the SAA1 locus is located on the same 350 kb NotI restriction fragment as the SAA2/SAA4 linked pair. The SAA3 pseudogene is not on this fragment although it has been mapped to the short arm of chromosome 11 (G. C. Sellar and A. S. W., unpublished) as has a putative fifth SAA gene (G. C. Sellar and A. S. W., unpublished). It is likely, therefore, that an extensive cluster of SAA superfamily genes, displaying different degrees of relatedness and different induction characteristics exists. The existence of such a cluster is supported by the close linkage on a syntenic region of mouse chromosome 7 of the two major acute phase SAA genes (SAA1 and SAA2), a minor acute phase gene (SAA3) and an SAA pseudogene (ψSAA), the first three being approximately analogous to their similarly numbered human counterparts. No C-SAA has been identified to date in mouse. However, an octapeptide in a position similar to that present in human C-SAA is present in the massively induced A-SAAs of a range of species including dog, cat, horse, and mink. When compared to the octapeptide-containing A-SAAs of other mammals, the human C-SAA presents a paradox since it is the only one which is constitutively expressed.

The differential expression of SAA superfamily members constitutes one of the best systems for the study of comparative control mechanisms in APR genes and their products. Woo et al. ((1987) J Biol Chem 262: 15790–5) have demonstrated that IL-1 can induce the expression of human A-SAA following transfection into mouse fibroblasts of a human SAA2 gene. It was subsequently demonstrated that the IL-1 responsive region of the SAA 2 promoter region contained a NFκB binding site and established that this transcription factor was intimately involved in controlling expression of the gene. Analysis of SAA expression in the human hepatoma cell line PLC/PRF/5 has shown that IL-6 can also induce SAA mRNA and protein expression, though not by the same magnitude as IL-1β. When IL-1β and IL-6 are used together they show a dramatic synergistic induction that is of the same magnitude and kinetics as that produced by monocyte conditioned medium, a relatively physiological stimulus. This established that for A-SAA, IL-1β and IL-6 in combination) are the cytokines that are both necessary and sufficient for maximum induction. These studies with PLC/PRF/5 cells have confirmed that the principal means of exercising control of SAA expression following an inflammatory stimulus is via increased transcription and the accumulation of mRNA. At the time when induced SAA mRNA levels are at their peak, however, the capacity of the cells to synthesize SAA protein is less than would be expected from a strictly proportional use of the absolute levels of accumulated SAA mRNA when compared with earlier times post-stimulus. This suggests a modulating role for post-transcriptional control. This modulation does not appear to be due to progressive variation in the A-SAA export capacities of the cells at different times post-stimulus, as is the case for CRP, or differential engagement of A-SAA mRNA by the cellular translation apparatus, i.e. ribonucleoproteins, monosomes, and polysomes, as is the case for ferritin heavy and light chain mRNAs. Although the cellular levels of A-SAA mRNA decrease rapidly after reaching their peak, the A-SAA mRNA itself is intrinsically stable. Our current efforts to define the biosynthesis of A-SAA are focused on the mRNA poly(A) tail which shows a progressive, controlled shortening from the length present at the time of the appearance of induced mRNA concentrations: this may affect specific mRNA degradation processes and/or the efficiency of its translation. In contrast to A-SAA, C-SAA is minimally induced by IL-1β and IL-6. Although its genetic organization is grossly the same as that of the A-SAA genes the sequence and motifs contained in its promoter region and introns are radically different. A comparative analysis of A-SAA and C-SAA promoter activity will be useful in further defining the intrinsic genetic elements required for the induction of major APRs. SAA and SAP are archetypal examples of plasma proteins that are beneficial in the transient acute phase response but that have detrimental effects in chronic inflammation. The causative or associated involvement of these major acute phase proteins in a number of clinical conditions has been implicated directly or circumstantially as outlined briefly below.

Secondary, or reactive, amyloidosis is the occasional consequence of a number of chronic and recurrent inflammatory diseases (Cohen, et al. (1959) Nature, 183: 1202–3), for example leprosy, tuberculosis, systemic lupus erythematosus, and rheumatoid arthritis. It is characterized by the ultimately fatal progressive deposition of insoluble fibrils in a variety of tissues including spleen, liver, and kidney. Secondary amyloid deposits are composed principally of amyloid A (AA), which is derived, probably by proteolysis, from the precursor SAA, in association with amyloid P component (AP) which is the localized form of SAP. The pathogenesis of secondary amyloidosis is poorly understood, however AA is deposited as β-pleated sheets and AP, which has been shown to be capable of acting as an elastase inhibitor, may protect the deposits against degradation by proteolytic enzymes. Alternatively, SAP may act as a nucleating agent in fibril deposition via its binding to fibronectin. Whatever the precise mechanism it is clear that high circulating and local levels of SAA and SAP such as those that are maintained in mice undergoing chronic experimental inflammation are likely to contribute to amyloidogenesis. Although not a major APR in humans, as mentioned above SAP may be induced locally or systemically by different combinations of cytokines. Recent studies have shown that there is a dynamic interchange of SAP between the circulation and the deposits in patients with secondary amyloidosis and there are anecdotal reports of regression and even disappearance of deposits in some patients. It is therefore important to devise strategies to down-regulate specifically SAA and/or SAP during chronic inflammation not only to halt or slow down the progression of amyloid deposition, but to reduce the concentration of these major APRs to below an 'amyloidogenic threshold' and permit the action of physiological corrective and clearance mechanisms, they exist, to predominate.

The association of SAA with HDL3 suggests another area in which chronic high SAA concentrations may promote clinical disease. Elevated HDL levels correlate inversely with susceptibility to atherosclerosis. HDL is central to the process of reverse cholesterol transport, and there is a significant decrease in plasma HDL cholesterol during inflammation. It is likely that during inflammation the association of A-SAA with HDL modifies the particle and equips it for a protective host defence role for which there is an overriding short term requirement. High SAA levels on HDL3 are achieved at the expense of apolipoprotein AI, the associated concentration of which is much reduced. HDL is the major substrate for lecithin-cholesterol acyltransferase (LCAT), one of the critical enzymes involved in cholesterol esterification. As apolipoprotein AI is required as an activator for the LCAT reaction. A-SAA may interfere with this reaction by displacing apoAl (directly or indirectly) from the HDL particle which could radically alter HDL metabolism during inflammation. Thus SAA may diminish the functional capacity of HDL for reverse cholesterol transport. We would further speculate that C-SAA on normal HDL contributes to its normal physiological role in reverse cholesterol transport. The chronic persistence of A-SAA on HDL in chronic inflammatory diseases could compromise the function of HDL over significant periods of time. Together with the concomitant sustained decrease in total HDL this would constitute a major risk factor for the development of atherosclerosis and could provide a molecular explanation for the increased mortality from cardiovascular disease observed in patients with active systemic rheumatoid arthritis.

Recently the rabbit SAA3 molecule has been shown to be a product of synovial fibroblasts that can be induced with either phorbol esters or IL-1. The rabbit SAA3 appears to function as an autocrine collagenase inducer. As collagenase is the central component involved in the enzymatic breakdown of collagens I, II, and III in the connective tissue of rheumatoid arthritis and osteoarthritis patients, some SAAs may play a critical role in the pathogenesis of these diseases. If other SAA superfamily members are also local or systemic signal molecules, the rapidity and magnitude of their induction suggests that they would be important in driving the acute phase response and in mediating the continuation of potentially detrimental processes in chronic inflammation.

In summary, a thorough examination of the structure, expression, and molecular genetics of all of the members of the SAA superfamily is likely, therefore, to be of considerable clinical, as well as biological, importance.

The acute phase response represents a radical departure from the normal metabolic processes that maintain homeostasis. The ability of an organism to respond quickly and effectively to a physical challenge has evolved as a short term survival strategy. The many physiological changes that take place immediately following such a challenge are initiated, maintained, and coordinated principally by a complex network of cytokines. These cytokines act in concert to modulate their own synthesis and to alter the metabolic and biosynthetic profiles of some of the major systems of the body: immune, haemopoietic, CNS, and the liver. The combined effects of the acute phase is to neutralize the pro-inflammatory actions of the stimulus; to physically kill and/or remove the stimulating agent and the tissue debris generated by the stimulus; to promote tissue repair; and to facilitate a rapid return to homeostasis. Researchers are only now beginning to understand the complexities of the acute phase response and flexibility of the reaction elicited by a range of stimulating agents and to realize that it is of great clinical as well as scientific interest. Considerable effort will continue to be made to define the parameters that shape the acute phase response more completely in order to be able to optimize the treatment of infectious disease and trauma. In addition, we need to discover more about the mechanisms whereby some acute phase processes continue to act, with devastating medical and social consequences, in chronic inflammatory conditions.

4.6.3 Interleukin-1

Interleukin-I (IL-1) is the term for two related proteins, IL-1α and IL-1β, produced by activated macrophages and many other cells. Although both forms of IL-1 are distinct gene products, they are recognized by the same cell surface receptors and are similar in function. Historically, IL-1 was discovered as an endogenous pyrogen and later identified as a co-stimulator promoting the growth of lectin-stimulated thymocytes. IL-1 is now considered to be a central mediator of host responses to infection and other forms of trauma. The many regulatory roles attributable to IL-1 include the control of cellular and humoral immune responses, inflammation, fever, acute phase responses, and haemopoiesis. Its biological effects are not restricted to a particular cell lineage, but instead IL-1 is a multi-functional cytokine acting on a variety of cells both within the immune system and other cellular systems.

IL-1 forms, together with two other peptide hormones, namely IL-6 and TNFα, a group of cytokines that are expressed during infection and particularly in infection with Gram-negative bacteria. The biological properties of IL-1 share remarkable similarities to those of TNFα, most notably the induction of fever, inflammation, and haemodynamic shock. Nearly all responses to either IL-1 or TNFα can be enhanced when the two are administered together. IL-6, like IL-1 and TNFα, increases synthesis of acute phase proteins and causes fever. Thus, although this review focuses on IL-1, the reader should keep in mind that IL-1 is part of a cytokine network in which its expression and biological properties are influenced by IL-6 and TNFα.

Much interest has focused on IL-1 as a mediator in disease. Elevated circulating levels of IL-1 correlate with a variety of clinical situations including septic shock. Moreover, a role of IL-1 as a mediator in chronic inflammation can be inferred from animal and human studies and is particularly emphasized in acute rheumatoid arthritis. Thus, IL-1 can be viewed as a mediator of host defense as well as of disease.

Because of the potent and profound biological effects of IL-1 it is not surprising that its activities are tightly regulated, most notably at the levels of transcription, translation, and secretion. Additional regulatory mechanisms are provided by the concomitant action of other cytokines, differences in the expression of IL-1 receptors on target cells, and the production of natural inhibitory proteins, as for example the recently identified IL-1 receptor antagonist (IL-IRN) (Seckinger, et al. (1987) J Immunol 139: 1546–9). Moreover, understanding the exact mechanisms that regulate IL-1 activity in vivo requires consideration of additional parameters such as distinct micro-environment and anatomical compartmentalization.

Complementary DNA (cDNA) cloning, protein purification, and sequencing studies isolated two forms of IL-1, termed IL-1α (pI 5.0) and IL-1β (pI 7.0), which are present in several species including man and mouse (see Lomedico, et al. (1984) Nature 312: 458–62). The genes for human IL-1α and IL-1β have been sequenced and were localized to the long arm of chromosome 2. The size of the human IL-1α and IL-1β gene is 10.5 kb and 7.8 kb, respectively. Each IL-1 gene contains seven exons but they share only 45 per cent homology in their nucleic acid sequence.

The IL-1α mRNA is about 2.3 kb in length, whereas the reported size of the IL-1β mRNA ranges from 1.4 to 1.8 kb. Both IL-1 mRNAs are translated into polypeptides (271 amino acids for IL-1α and 269 amino acids for IL-1β) of approximately 31 kDa. However, the predominant molecular weight of the two IL-1 proteins in culture supernatants from macrophages and in biological fluids is only about 17.5 kDa. The data indicate that IL-1α and IL-1β are synthesized as precursor proteins which are subsequently modified to yield extracellular low molecular weight IL-1 polypeptides. Comparison of the N-terminal protein sequence data with respective cDNA sequences further revealed that, for both forms of IL-1, it is the carboxyl-terminal portion of the molecule that is present in culture supernatants as active IL-1. Receptor binding and full biological activity requires a minimum amino acid sequence spanning residues 128 to 267 in IL-1α, and residues 120 to 266 in IL-1β.

Human IL-1β has been crystallized and the structure analysed by nuclear magnetic resonance spectroscopy. According to these studies, IL-1β presembles a tetrahedron and is composed of 12 β-strands arranged in three pseudo-symmetric topological units.

At the amino acid level, the sequence identity between the IL-1α and IL-1β precursor as well as the extracellular forms of IL-1 is only in the order of 25 to 30 per cent. Yet, their biological activities are similar, and both IL-1α and IL-1β competitively bind to a common receptor on various target cells. Moreover, the two forms of IL-1 are structurally of particular interest, in that neither IL-1α nor IL-1β contains a secretory signal peptide as would be expected for a protein destined for secretion.

IL-1α and IL-1β arise by de novo RNA and protein synthesis. Although cells of the monocyte/macrophage lineage remain an important source for IL-1, IL-1 is now known to be produced by a large number of lymphoid and non-lymphoid cells. With the exception of skin keratinocytes, production of both forms of IL-1 is not constitutive, but is only transiently induced by various stimuli including other cytokines, complement components, immune-complexes, phorbol esters, bacteria, and several microbial products (for review see references Dinarello (1991) J Infect Dis, 163: 1177–84). The best studied of these is lipopolysacharide (LPS), which stimulates IL-1 production at concentrations as low as 10 pg/ml.

The two forms of IL-1 appear to be under separate transcriptional control. In human monocytes both IL-1 genes are transcribed within 15 minutes after stimulation with LPS. However, stimulation of the cells with phorbol myristate acetate (PMA) induces IL-1β, but not IL-1α transcription. Furthermore, a differential expression of IL-1α and IL-1β has been observed in various cell types.

The transcriptional activation mechanisms of the IL-1 genes are poorly defined. There is, however, evidence that activation of protein kinase C(PKC) is involved in signal transmission: PKC activating phorbol esters, (e.g. PMA) induce IL-1β expression in human monocytes, and LPS-induced expression of both IL-1α and IL-1β can be down-regulated by PKC inhibitors.

The production of IL-1 is also regulated at the level of mRNA stability and translation. Although the IL-Iα gene is transcribed in cultured (aged) monocytes there are no detectable levels of IL-1α mRNA in such cells, indicating that the IL-Iα mRNA is rapidly degraded. Moreover, adherence of monocutes to glass or plastic triggers IL-1 gene expression without translation into IL-1 proteins. The latter, however, can be induced by a second signal, provided by LPS or by the complement component C5a. Accordingly, it appears that transcription and translation of IL-1 are separately regulated.

The cytokines inducing IL-1 production include IL-1 (α and β) itself, TNFα, granulocyte macrophage colony-stimulating factor (GM-CSF), and macrophage-CSF. Suppression of IL-1 production has been observed in th presence of IL4, IL-6, IL-10, and transforming growth factor-β (TGFβ). IFNγ has a dual role, it augments IL-I production induced by LPS but suppresses IL-1 production induced by IL-1.

IL-1α and IL-1β mRNAs are translated into precursor proteins (pro-IL-1α and pro-IL-1β) of 31 kDa which are cleaved by proteases either during or after secretion. IL-Iα cannot be translocated across microsomal membrane. Immunoelectron microscopy as well as subcellular fractionation studies confirmed that neither form of IL-1 is detectable in the endoplasmic reticulum or in the Golgi apparatus. This clearly relates to the apparent lack of a N-terminal signal peptide. Therefore, all indications favour IL-1α and IL-1β as being cytosolic proteins.

Association of IL-1 proteins with other cell organelles has been reporte for lysosomes and mitochondria. A number of studies suggest that IL-Iα, but not IL-Iβ exists as a membrane protein on activated macrophage initially, membrane IL-1 was detected by measuring IL-1 activity on paraformaldehyde-fixed murine macrophages. Later it has been shown that most of the measured bio-activity was probably due to the leakage of IL-1α out of the fixed cells, indicating that fixation of the macrophages with paraformaldehyde is inadequate to prove the existence of a membrane form IL-1. However, IL-1 a was detected on the membrane of monocytes and macrophages, using fluorescence labeling and cell surface iodination. The mechanism by which IL-1 a may be anchored to the membrane remains to be determined. The IL-1α precursor is phosphorylated at serine residue 90 and phosphorylated pro-IL-1α binds to membrane vesicles of monocytes in the presence of calcium. Thus, phosphorylation could serve as a mechanism, facilitating the interaction of pro-IL-1α with cell membranes. Alternatively, anchoring of pro-IL-1α to the membrane has been proposed via lectin-like binding because D-mannose dissociates the pro-IL-1α from the membrane.

It is unclear how IL-1 is transported out of the cells and how it is cleaved to its bio-active peptides. IL-1α can be released from intact macrophages by trypsin-like enzymes and it has been proposed that membrane IL-1 is a prerequisite for secretion of IL-1α, since a calcium-activated neutral protease has been described to process pro-IL-1α. The secretion of IL-1β from macrophages occurs much earlier and faster than that of IL-1α, suggesting that the secretion of the two forms of IL-1 is controlled by separate mechanism(s). Pro-IL-1β lacks biological activity; it is secreted unprocessed and cleaved only later by various enzymes including elastase and plasmin. A monocyte-specific protease has been described that specifically cleaves pro-IL-1β at alanine position 117. Incomplete processing of secreted pro-IL-1β may be due to spontaneous disulfide-mediated protein folding.

cDNA has been cloned from a human monocytic cell line which encodes an enzyme which specifically hydrolyses the pro-form of IL-1β to the mature form. The enzyme has 404 amino acids and does not belong to any known family of proteases. The gene for the converting enzyme has been localized to chromosome 11 at the 11q23 band. This band has been identified as being frequently involved in rearrangements in human leukaemias and lymphomas and it has been suggested that this enzyme may have a functional role in regulating cell growth.

The various biological activities of IL-1 are mediated by specific receptors on the surface of many cells (Bomsztyk, et al. (1989) Proc Natl Acad Sci USA 86: 8034–8). The binding of IL-1 is specific and saturable and occurs with high affinity; $K_d$ in the order of $5 \times 10^{-10}$ to $5 \times 10^{-11}$ M. To date, two distinct single chain receptors have been identified: one of 80 kDa is designated IL-1 receptor type I (IL-1R type I) and is expressed on T cells, fibroblasts, and epithelial cells (Sims,et al. (1988) Science 241: 585–9); the other of 68 kDa is called IL-1R type II and is expressed on B cells, neutrophils, and macrophages. Both types of IL-1R have been cloned and sequenced and belong to the immunoglobulin (Ig) superfamily (Dower et al. (1990) J Leukoc Biol 1: 103–7). Besides being expressed on different cells, the two IL-1R differ with respect to their binding affinities and regulation of surface expression. Although IL-1α and IL-1β are equally recognized by the IL-1R type 1, IL-1α binds better to the type I receptor whereas IL-1β does so to the type II receptor. In fact, there is evidence that IL-1β triggers B cells in vivo whereas IL-1α does not. In this context, it has been suggested that IL-1α may act as a competitive inhibitor of the immunostimulatory properties of IL-1β. The molecular mechanism by which a signal resulting from IL-1 binding to its receptor is transduced intracellularly is not completely understood.

Many of the biological properties of IL-1 attest to its having a fundamental role in both non-specific immunity and specific immunity in the host defence against infection. When administered into animals, IL-1 induces a series of physiological changes mimicking the acute phase response to infection (Dinarello, et al. (1988) Rev Infect Dis, 10: 168–69). These changes including fever, increased synthesis of acute phase reactants in the liver and reductions in plasma iron are thought to be beneficial for the host by increasing opsonization of micro-organisms and by inhibiting microbial growth IL-1 induces gene expression of neutrophil and monocyte chemotactic cytokines such as IL-8, IL-9, and macrophage inflammatory proteins which, in turn stimulate neutrophil migration and degranulation in vivo. Also, IL-1 induces the expression of adhesion molecules which promote neutrophil and lymphocyte adherence to the vascular endothelium. These effects on endothelial cells are clinically important in that they limit the spread of infection and also allow leucocytes to pass and be retained at the site of inflammation Thus, if synthesis and secretion of IL-1 represents a first line of defense against acute infection, its local and systemic effects may help to mobilize non-specific defense mechanisms.

To evaluate IL-1 for its capacity to mobilize antimicrobial resistance animals have been treated with IL-1 in a variety of infectious disease models. When injected in a low dose, IL-1 appears to protect mice from lethal infections due to bacteria, and parasites. In most cases, maximal enhancement of survival following acute infection was observed when IL-1-treatment preceded infection by at least 4 hours. The mechanism(s) by which IL-1 enhances antimicrobial resistance remains to be further elucidated Although IL-1 treatment clearly induces neutrophilia a decrease in the number of pathogens is not detectable in all models, suggesting that IL-1-induce protection is not only due to increased microbicidal mechanisms.

In Gram-negative bacterial infection detrimental and even lethal effect are mediated by TNFα, the receptor expression of which is down-regulate by IL-1. Accordingly, IL-1-induced protection is likely to involve desensitization due to the action of TNFα. In addition, there is evidence that IL-1-induced suppression of parasitaemia in murine cerebral malaria is least partly mediated by IFNγ released by T cells.

Cell-mediated immunity plays a major role in host defence against intracellular pathogens. One of the cytokines required to enhance the anti-microbial activity of infected macrophages is IFNYy produced by activated T cells. All indications favour IL-1 as being an important component in the activation of a subset of T helper cells designated $T_H2$ cells. However, IL-1 only serves as a co-stimulator to induce IL-2 and IL-2R expression in the context of antigen presentation.

Extracellular pathogens are usually adequately dealt with by antibody-mediated mechanisms. IL-1 is a co-stimulator for B cell activation and Ig production and it particularly acts together with IL-4 and IL-6, and thus contributes to the antibody-mediated anti-microbial defence.

To gain further insights into the action of IL-1 during infection several questions need to be answered. Firstly, which cells produce IL-1 (α and β) and when do they do so. Secondly, does the micro-environment affect the expression of IL-1 genes. Thirdly, do the IL-1 producing cells also synthesize TNFα and IL-6. Fourthly, which cells have receptors for IL-1 in normal and diseased tissue.

To investigate the induction of IL-1 at a local site of infection we have used the mouse model of yersiniosis. The advantages of this model of infection include the ability of *Yersinia enterocolitica* 08, an enteropathogenic bacterium, to preferentially invade the Peyer's Patches of the distal ileum after oral infection. The localization of IL-1α and IL-1β producing cells by immunoperoxidase staining of adjacent tissue sections of Peyer's Patches prepared from mice after six days of infection reveals a clear distinction between cells recognized by the antiserum to either IL-1α or IL-1β. IL-1α producing cells are mature macrophages while IL-1β producing cells are monocytes (Beuscher, unpublished). When comparing the kinetics of appearance of IL-1α and IL-1β immunoreactive cells, it is clear that the induction of IL-1α is delayed by at least 24 hours. In addition, production of IL-1α and IL-1β in inflamed Peyer's Patches does not originate from resident cells, but rather from monocytes migrating from the circulation into the tissue. We conclude from these results that the differential production of IL-1α and IL-1β is controlled by the differentiation of activated monocytes to activated tissue macrophages.

Elevated circulating levels of IL-1 and TNFα have been reported in patients and animals with sepsis due to a variety of micro-organisms, and the relative amounts of both cytokines correlate with the degree of hypotension during lethal bacteraemia, indicating that under these circumstances IL-1β and IL-6 are under the control of TNFα. These data emphasize the importance of IL-1 and TNFα for the development of the septic shock syndrome. Thus, substances that would allow a co-ordinated modulation of IL-1 and TNFα activities would be of potential benefit as therapeutic agents.

There are several currently understood strategies for inhibiting IL-1 activity. As reviewed elsewhere, reduction or prevention of IL-1 synthesis by either corticosteroids or agents that block the lipoxygenase pathway of arachidonate metabolism may provide an important approach to anti-inflammatory therapy. In addition, cytokines such as TGFβ, and IL-10 may also be useful to reduce IL-1 synthesis.

Inhibition of IL-1 already released into circulation, as for example during septic shock, requires a separate strategy. IL-1R blockade with antibodies to the IL-1R type I has been shown to attenuate the host inflammatory response and protect mice from LPS and IL-1-induced acute inflammation. In addition, administration of the extracellular domain of the IL-1R type I (soluble IL-1R protein) to animals seems to decrease inflammatory responses). Antibodies that specifically bind to IL-1 have not been tested so far, but antibodies to TNFα were shown to protect mice from endotoxaemia and *Escherichia coli* sepsis.

The existence of naturally occurring inhibitors of IL-1 activity has been firmly established in vitro and in vivo. These inhibitors can be divided into two groups, one of which consists of substances, e.g. $α_2$,-macroglobulin and lipoproteins, that inhibit IL-1 activity, but they also interact with other proteins not related to IL-1. The second group consists of polypeptides that specifically inhibit IL-1 activity. A member of this group of IL-1 inhibitors has recently been cloned and termed IL-1R antagonist (IL-1RN). The cDNA sequence codes for a polypeptide of 17–3 kDa. Similar to the naturally occurring IL-1RN polypeptide (23 kDa), the recombinant IL-1RN binds avidly only to IL-1R type I and appears to prevent signal transduction by directly blocking the binding of IL-1 without inducing a signal of its own. Comparison of the deduced protein sequences and intron-exon organization of the genes for IL-1α, IL-1β, and IL-1ra indicate that the three IL-1R ligands have a common evolutionary ancestor.

In animal models, administration of IL-1ra prevents death from endotoxin shock and reduces *E. coli*-induced hypotension. In addition, IL-1ra blocks IL-1-induced $PGE_2$ synthesis from synovial cells and collagenase synthesis from chondrocytes.

IL-1 is a multi-functional cytokine closely related to IL-6 and TNFα. IL-1 mediates inflammatory reactions, activates B and T cells, and stimulates haemopoiesis. In addition, IL-1 is a major inducer of IL-6 and TNFα, which reinforces the synergistic action of the three molecules.

Molecular cloning of IL-1 has led to the characterization of two distinct IL-1 proteins, i.e. IL-1α and IL-1β, which share a similar spectrum of activities. IL-1α and IL-1β appear to be differently expressed in certain cell types and also differ in their binding affinities to IL-1 receptors expressed on T and B cells, respectively. However, at present it is still difficult to understand the significance for the existence of the two forms of IL-1.

4.6.4 Therapeutic and Prophylactic Compounds

Compounds identified above as being useful for preventing IL-1 mediated inflammatory processes, can be, e.g. a nucleic acid (e.g DNA, RNA or PNA), protein, peptide, peptidomimetic, small molecule, or derivative thereof Preferred compounds are capable of binding to, and inhibiting transcription, translation, processing, or activity of an IL-1 gene or protein. Examples include antisense, ribozyme or triplex nucleic acids, small molecule ligands, antibody or antibody-like binding fragments. Alternative compounds are competitive inhibitors of a protein involved in IL-1 mediated inflammation, such as a portion of human or mouse IL-1 sufficient to bind to an IL-1 type I receptor and interfere with binding of IL-1 alpha and beta proteins on the surface of a cell.

Toxicity and therapeutic efficacy of such compounds can be determined by standard pharmaceutical procedures in cell cultures or experimental animals, e.g., for determining the $Ld_{50}$ (The Dose Lethal To 50% Of The Population) and the $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possiblity of local noninvasive delivery of drugs over an extended period of time, This technology utilizes microspheres of precapillary size which can be injected via a coronary chatheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

In situations in which the therapeutic is a gene, a gene delivery system can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) PNAS 91: 3054–3057). A therapeutic gene, such as a gene encoding an antisense RNA or a ribozyme can be delivered in a gene therapy construct by electroporation using techniques described, for example, by Dev et al. ((1994) Cancer Treat Rev 20:105–115).

A gene therapy preparation can consist essentially of a gene delivery system in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

EXAMPLE 1

Preparation of Knock-out Construct and Knock-out Mammals

We generated a population of mice that contain an inactivating deletion of the interleukin-1 receptor antagonist (IL-1RN) gene. Deletion of the gene was effected by deleting from the EcoRV site in exon 3 to the first XbaI site in exon 4, which is downstream of the translational stop codon. The knock-out construct was a circular plasmid which when linearized with NheI mapped as follows:

NheI corresponded to position 916 of the sequence (intron 1). The first IL-1RN-homologous segment ran from position 916 to the EcoRV site at position 3530. The interruption broke off the transcript at codon 100 of the proprotein, leaving only half of the coding sequence for the mature IL-1 receptor antagonist intact. Given the structure of IL-1 receptor antagonist (a single folded domain in which interspersed parts of the sequence support the structure of the protein), we surmised that it was highly unlikely that a protein product of this transcript could be functional.

The linearized marker sequence (total length of 4.4 kb) contained, in order, 1) a linker sequence containing an in frame translational stop codon; 2) an inverted marker gene consisting of a beta-actin promoter driving aminoglycoside phosphotransferase (aph) a/k/a the neomycin, kanamycin or G418 resistance gene; 3) the body of the plasmid including the beta-lactamase gene (ampicillin resistance for plasmid selection in *E. coli*); followed by 4) the linker sequence. The marker sequence was followed by the rest of the IL-1RN gene, beginning at the XbaI site at position 4791. The second homologous portion ran from position 4791 in exon 4 to an NheI site beyond the end of the sequenced DNA of the gene. The NheI site mapped to about 11800 using the numbering of Zahedi, el al., supra. Thus, the total homologous sequence was 2.5 kb+7.0 kb=9.5 kb. In the circular plasmid the two NheI sites were united, so that linearizing the construct yielded transfectable knock-out construct without the need to separate away any part of the plasmid.

The linearized knock-out construct was transfected into ES cells (129/Olac) by electroporation and transfected cells were selected by incubation in the antibiotic G4 18. Positive cells were injected into MF1 recipient embryos. Chimaera were identified and crossed with an outbred albino line (MF1). Transgenic heterozygotes were identified and crossed to each other to produce homozygous mice. Since then, all animals have been inbred.

EXAMPLE 2

IL-1RN Knock-out Mammals

We have studied a population of IL-1RN knock-out homozygotes looking for evidence of inflammatory conditions. One prominent condition was that of extensive arteritic lesions as described below. However, study is ongoing to identify other inflammatory pathologies.

In normal animal house conditions since at least about one year, we bred a population of 60 homozygous animals and 56 heterozygotes. A group of 40 homozygotes and 54 heterozygotes have been followed to 300 days from birth. During that period, 2 heterozygotes (5%) and 42 homozygotes (78%) have died or been terminated due to illness. The median age of death of the homozygotes was 156 days. Autopsies were performed on 40 of the homozygous mice and 36 clear examples of arteritis were found, with 15 having died apparently through hemorrhage from ruptured aneurysms. In total, 85 homozygotes and 5 heterozygotes have died spontaneously or have been terminated to prevent suffering. Looking at all homozygotes that have been subjected to autopsy, whether killed prospectively, terminated due to illness or spontaneously dying, 43 of 48 have been found to be suffering from arteritic lesions.

The arteritis observed had the following features similar to human giant cell arteritis:

It affects large and medium vessels and is widely distributed.

It shows collapse and disappearance of the elastic lamina while the intima is not affected.

A massive inflammatory infiltrate is seen across the entire vessel wall.

Lesions are found to be focused at the branches, bifurcations and flexures of major arteries, including the coronary arteries.

We have detected arteritic lesions in 8 of 17 prospectively killed heterozygous animals examined so far, but no heterozygous animal has yet apparently died as a result of arteritis. The lesions are not severe, with evidence of repair and scarring, and no evidence of aneurysms. By contrast, no lesions have been found in 8 wild-type litter mates of similar age.

These findings show a key role for the IL-1 system in arterial homeostasis. In particular, unopposed IL-1 activity in mice who lack the capacity to produce the IL-1 receptor antagonist inhibitor of IL-1 activity, leads to pathogenic arterial inflammation that results in excess death rates in the homozygous IL-1RN deletion mutant animals. These animals will be valuable models for the discovery and testing of new and existing agents and other therapeutic approaches aimed at preventing arterial diseases, or halting the progression of arterial disease, or reversing the pathological changes of arterial diseases.

Likewise, these animals will be useful in studying agents that directly target the IL-1 gene products and the IL-1 cascades and in studying other inflammatory conditions with a strong IL-1 component.

What is claimed is:

1. A transgenic mouse, wherein said mouse carries a disruption in an endogenous interleukin-1 receptor antagonist (IL-1RN) gene in which at least 50 consecutive nucleotides of coding sequence of the interleukin-1 receptor antagonist gene have been deleted and wherein the mouse exhibits a phenotype selected from the group consisting of: the presence of an arteritic lesion, damage to the elastic lamina of a blood vessel, an inflammatory infiltrate across the wall of a blood vessel, arterial inflammation and an aneurysm.

2. A transgenic mouse of claim 1, wherein the mouse is heterozygous for the disruption in the interleukin-1 receptor antagonist gene.

3. A transgenic mouse of claim 1, wherein the mouse is homozygous for the targeted disruption in the interleukin-1 receptor antagonist gene.

4. A transgenic mouse of claim 1, wherein the disruption occurs from an EcoRV site in exon 3 to an XbaI site in exon 4 of the interleukin-1 receptor antagonist gene.

5. A cell or cell line from a transgenic mouse, wherein the cell or cell line contains a targeted disruption in the interleukin-1 receptor antagonist gene in which at least 50 consecutive nucleotides of interleukin-1 receptor antagonist gene coding sequence have been deleted.

6. A cell or cell line of claim 5, which is an undifferentiated cell.

7. A cell or cell line of claim 6, wherein the undifferentiated cell is selected from the group consisting of: a stem cell, embryonic stem cell oocyte and embryonic cell.

8. A cell or cell line of claim 5, wherein the disruption occurs from an EcoRV site in exon 3 to an XbaI site in exon 4 of the interleukin-1 receptor antagonist gene.

9. A method of producing a mouse with a targeted disruption in an interleukin-1 receptor antagonist (IL-1RN) gene, comprising the steps of:

a. creating a knock-out construct comprising a portion of the IL-1RN gene with an internal portion of said IL-1RN gene replaced by a marker, wherein at least 50 consecutive nucleotides of IL-1RN gene coding sequence have been deleted;

b. transfecting said knock-out construct into a population of embryonic stem cells and selecting a transfected ES cell which expresses said marker;

c. introducing said transfected ES cell into an embryo of an ancestor of said mouse;

d. allowing said embryo to develop to term to produce a chimeric mouse with the knock-out construct in its germline;

e. breeding said chimeric mammal, to produce a heterozygous mouse with a targeted disruption in the IL-1RN gene.

10. An IL-1 receptor antagonist knock-out construct, comprising a portion of an interleukin-1 receptor antagonist (IL-1RN) gene, wherein an internal portion of said IL-1RN gene is replaced by a selectable marker and at least 50 consecutive nucleotides of IL-1RN gene coding sequence have been deleted.

11. The IL-1RN knock-out construct of claim 10, wherein the selectable marker is a gene encoding a protein selected from the group consisting of: thymidine kinase, neomycin phosphotransferase and hygromycin B phosphotransferase.

12. The IL-1RN knock-out construct of claim 10, wherein the internal portion is flanked by an EcoRV site of exon 3 and an XbaI site of exon 4 and wherein the marker is a neomycin resistance gene.

13. A method of testing an agent for effectiveness against an inflammatory and/or cardiovascular condition, said method comprising:

a. obtaining a transgenic mouse that is homozygous for an interleukin-1 receptor antagonist null allele wherein the transgenic mouse exhibits a phenotype selected from the group consisting of: the presence of an arteritic lesion, damage to the elastic lamina of a blood vessel, an inflammatory infiltrate across the wall of a blood vessel, arterial inflammation and an aneurysm, and b. administering said agent to said transgenic animal;

wherein an agent that ameliorates said phenotype is selected as an agent that has effectiveness against said condition.

14. A transgenic mouse of claim 1, wherein the phenotype includes an arterial disease having an inflammatory component.

15. A transgenic mouse of claim 14, wherein the phenotype includes damage to the connective tissue of an artery.

16. The transgenic mouse of claim 1, wherein the mouse is derived from an MF1 mouse line.

17. The transgenic mouse of claim 4, wherein the mouse is derived from an MF1 mouse line.

18. The method of claim 9, wherein the ancestor of said mouse is an MF1 mouse.

19. The method of claim 13, wherein the mouse is derived from an MF1 mouse line.

20. The method of claim 13, wherein the interleukin-1 receptor antagonist null allele is a deletion of at least 50 consecutive nucleotides of coding sequence of the interleukin-1 receptor antagonist gene.

21. The method of claim 13, wherein the interleulin-1 receptor antagonist null allele is a disruption from an EcoRV site in exon 3 to an XbaI site in exon 4 of the interleukin-1 receptor antagonist gene.

* * * * *

SEQUENCE LISTING

```
<160> NUMBER OF SEQ ID NOS: 2

<210> SEQ ID NO 1
<211> LENGTH: 6350
<212> TYPE: DNA
<213> ORGANISM: mouse

<400> SEQUENCE: 1
ggatctggtt ttttttggg ggggaggggg atcgggacag ggggatcagc aaatagactc      60
ggagtacctg tcatgcaaat gagggagtct ggttttcatt gtgctcttct tcccaggaac    120
accatgaagg ggaaacagag aacttaattt tggggaaatt acacagggta aggggagga    180 gatcagttac aacacaccat tgcgacactt tcagggttga cagcgacagc agtaaaggtt    240 tctcttttg gaaatatgag ggtttttccg cttctgacag tggaacggaa tgacagcagc    300
acaggctggt gaatgactac tttctttata agcaaccacc ttgagcctga aatggcagtc    360
gctagtctct attgccttgc tgtggcctcg ggatggaaat ctgctgggga ccctacagtc    420
acctaatctc tctccttctc atccttctgt ttcattcaga ggcagcctgc cgcccttctg    480
ggaaaagacc ctgcaagatg caagccttca ggtaagtctt ccaaagacac aggattgcat    540
agaccaagga ccagagacac atgccatatg tccagagcat atgcaggaat aggagatata    600
tatacatgta taatatatat aatgcgtgtg tgtatgtgtg tatacacata tgtatgtatg    660
tatgtgtata tatatatata tatatataat gtgtgtgtat acacatatgt atgtatgtgt    720
```

-continued

```
atatatatat atatatatat gtgtgtgtgt gtgtgtgtgt gtgtgtatcc ttgattcaag    780
aacagcatgc taaatgcagt ctttaagtct tatgttttaa aatattccat gcatggacaa    840
caagacagtt aactgtgctc actttctcag acacctagat gttcagtaag tgatggacag    900
gcatccggga ataatgctag ctttgggatc gagcaaagag gaatacttca gcaggacaca    960
gtcaaaggct cagaccaaca gtctacactc tgtatctgtg ttgacttgga agatatctct   1020
cgttggagtc cccagtttcc ttatctgtaa catgatactg ctctgatgat aaccccttgt   1080
gtgccttaca gggtgaacac taaatacatg agtgatactg taaccatgtt ctgagaccta   1140
tgctctgaga actgtaaagt gcctgaaaaa taacctgagt tttaaaaatt ggatcaaaag   1200
ccttgggaga tgccatcaac cttatagtaa aaatggcagg cctcgatttt gattttaaaa   1260
tgaataaaga gattgttggt gcatatgatc tgttcttgat ccttcctgag agtgaagtct   1320
gtgttgagtc acttccccct tgaccctgtc tgctttggat ccacagctgg aggctgggac   1380
tctaactgtg attctataca tctatcccaa ggcaagtctg tcccacagat ccagtaactg   1440
cttcgtgaga tttaccatca tcacatcctc ttagcagcct caagagagt ccctggagtc   1500 ctgttagcaa gactattgag tcccttgagt ttgaagctca ccagagatat agacaccagt   1560
cacaaaggca caaatactct ttcacgtgca gagtacttgg tttgtcctcc acccatccct   1620
gagctcctag gctgctccaa gctactcaaa aagtcctgtc agctctgctg accaggtaaa   1680
gagataaggg acagatccaa ggtcatatca tcaggcctct taccacacct cacaggtgcc   1740
tgcctctctg gaagccagag ggcctttcac caagaagtca gagagtaaca aacaggccct   1800
ggctgagcta gacaggaagc tgacttattt ccaaggacag ctgtccctgt caggcccaga   1860
gcagatggtc ccacaagagg ttttagttgt agacttgcag gtctaagtag agtagcttga   1920
ggtaggagta gtgaagccag actagcttgg ctacaataca ttctaaccct tgaacctgta   1980
acactatgat gtggtggcca cgagctacaa gtggccatct aaatttacac ataaacgcat   2040
gaaagcagaa gaaagtcctg tacctggcaa ctctatttag tggagtgact ataggatgtg   2100
cttgcatcgc ctaagtttct atcagatgct gacgctctat agaaaattct gctaaagtca   2160
tggatgtcca tgctgggatt ctgaggtgag gaacaagaaa agagggttt ctgttcacca   2220 gatgtgagag atgggctcat ttcttacatg gtatttgctt aaatcttccc atttgtgtta   2280
tgaacttggt aagtacgaca cttccagcaa gtctagatgt aaattaggtg actctgagga   2340
agctggaaag ggctctgtac tgcctactcc agctaggcca ttttgctttt cagaatctgg   2400
gatactaacc agaagacctt ttacctgaga acaaccagc tcattgctgg gtacttacaa   2460
ggaccaaata tcaaactaga aggtgagtgg ataacaggga agctggtgta atatggacat   2520
agagtccttt gccctgctcc tctgcctgga ggtgggatgt cctcatttct gttgagttgg   2580
aaatgagaga tttgaccacc aggggacata tgggagtggc ctcaagagag cagaaaagat   2640
aaagactggg tcacaatgct ccagggacac agctgagagg aacagaggcc agaaggcacc   2700
cgggcacctc cttagtcctt ctgtgctggt agtccactat accccagtgt tattcgaact   2760
ctacccttgc cctaggctaa tataacatgt atgtgggctg ggtagcattt ttactgtgga   2820
caccaccctc atcatgtacc ctctaaacta ggacaaagcc acatgaactt ggaggagcat   2880
tacccacaga ttcttcagtt tttcttagtt caggcactta gttgacagaa tctctgtttg   2940
tgagggaacg aagcattact tgtatctcct caggatcccc caagccttct gctttcctgt   3000
atcactcagc agttatgcaa ctggcttttc ctgtctttct agtaattctc ccatgaacac   3060
actcaagcat agaaggtgct ggcttctat tgctacccag taacaggatg gaaaggtgaa   3120
```

```
ctgtgtggaa cctattcatg ggccttgtga gcttttgtgc ctctgtctac taacagcaaa    3180
tctgttgact tggaggtctg gttcactgta gaaagtaaag gaaagttggg agcagtgtag    3240
aatctaggaa gctggtcctt acatagagtg tgctcatttg gatcttttgc ttggaggcag    3300
actagaaaga tagagccttc ttgaccttct tgaccttcta gttttataaa aggaagaca     3360 gaaaatacac acagacgctc ccctacccct gcctcctctt ctctctttct gacaccatcc    3420
tctactcttc tccagaaaag atagacatgg tgcctattga ccttcatagt gtgttcttgg    3480
gcatccacgg gggcaagctg tgcctgtctt gtgccaagtc tggagatgat atcaagctcc    3540
agctggaggt aagaatctgg tttagctatc aaatccttct aaaacccaat ggttatgaca    3600
acctcaggtg tttctcataa ccctgagcat gcaaagatga gggaggcttt tccttcttca    3660
cagagtacta ttttgaggtc actccttaag cagtttccac aatgttcttg gttgatattg    3720
ggtgtccaag gtggtttctc attctctcaa ctacccttta cgtaacttct ttgcattcag    3780
tcaacactct gagcttcctt aagcgtggtg accaactttt atgagagatt gttccagaaa    3840
gatgagcctc aatgtgaaag tgcttattaa gcttgggctt atgtaagtct attggcagaa    3900
gcctgtgacg tggttgatat ggactcattg tagaaaggta ctgcacaagg atctaaactt    3960
taggaggaga catggtcatt agaggagcac gacctgaacc accatgggtc ttgtgcctcc    4020
taaaccagtt gagcctacct tcttctagca aggtcaattc tcaagactat acactcccaa    4080
gcatcatcta tgctatttat tatctacgct cctaatttac atcccacaca gacctgtgtc    4140
acttactcct ttacctagtc agtagtaatg ggctgttcaa acattatctt gagggattag    4200
ctggacaaac ttttaatcca actgcaaata gccacaagca tgagtttgtt gataactctt    4260
accaatggac aggaacacct tttagaggac tttctcagcc ctcggcaatt acctgaccat    4320
ttcttgactt ccaggaagtt aacatcactg atctgagcaa gaacaaagaa gaagacaagc    4380
gctttacctt catccgctct gagaaaggcc ccaccaccag ctttgagtca gctgcctgtc    4440
caggatggtt cctctgcaca acactagagg ctgaccgtcc tgtgagcctc accaacacac    4500
cggaagagcc ccttatagtc acgaagttct acttccagga agaccaatag tactgccgag    4560
gcctgtaata atcaccaact gcctgatcac tctggccatc attggggcct gaggaacaac    4620
ttttgcaggg tgtacagtag aaggagacag aagagttctg atgatagatc tctgcctcag    4680
tctgttggct ggcctaatcc ccatgatgat tccagaataa tcttgcaaat tggatcatgg    4740
caggtgcttg ttcaaagccc tttcttgttg cctctgccat ctgggtgaag tctagaccac    4800
ttgcttggcc taggtgtctt ctgctctacc acccacccta ccctgccac aaacacacac    4860 tttttttgtt tttgtttttt ccattgttct gcacttccac agtccagacc aatcaagtca    4920
cttgacaata tgccccaagt gactcccta ccctgtttta taaacctgtg cctgtctatg    4980
gagaaggttt taattctcct tgttattcat tttgggcttt ttgatgaaac caccagggca    5040
tcacatatac taagcatgtg ctctaccatc atgttatgct tccagctcag gggggcactt    5100
ttaaggatct agaaaacaga aattaaggat ctcatagtta ttttattagg ccagccttat    5160
tccatgtcgg caagaggttt cttgtggaaa ttatgtcctt tctgagagga gctggggatt    5220
agatgctcct gcatttgtga aatggttata agcatagaaa aataggtggt aagctttcct    5280
tctttcctta ttttgtgtga tgccttaaac tgaaaagtta aaaattgatg gattgtagca    5340
ttcccataat ctcccccttc tttttttttc ctttggaaat gtccaatagt ctatattcct    5400
ctgtcccgcc caaacaccat cttcactcca agcctaccac agatgcctga agaagttcct    5460
```

-continued

```
cactatctgc aaatgtggct ctcaggccct tcctgatgtg atgaatgaat ctactaatca    5520
tttcttgacc gttcatttta tcacttctaa ccttgaaaca tgtggaagta gctatgttcc    5580
taactgtttc tctgccaga caatgaactc tggagatcag ggagcttcgt gtgtgtgtgt     5640
gtgtgtgtgt gtgtgtgtgt gtgtgtgtgt gcgcgcgcgc acgtgcatgc acatgctacg    5700
tattgggtcc ctccaaggat gaaccctctc tttggcttag aaggcactca gagaatatgt    5760
gttattcgtg ctcacggaaa gtttcttact catccctgtg actttggctt tattttacaa    5820
taaaacactg aaaatgtcca ctttgttagt tgtgaacatg agcccaggcc taaggtgctg    5880
ggaaacagaa agggcgggag attttttcttt attctatggc tagaaaatag ttacctcctc   5940
tctgaaagtc ttcttcctca tttctgggta acagaatatc aaacaccttg cttataagtt    6000
ataaagtagt gttgtccacc atgaacccac caagtaaaaa caacccaaat acctatcatg    6060
gatgaataat catgcaagta tcagatctgc actcaatgcc acacaatgac aaagatagca    6120
aatgagccac agacggctcc acccaaccca atagatgaac acttggttca aaatcactaa    6180
agctcaaata ctcccaggtc aaacaccagg taacaagtta atactcaaca aagggggaa     6240 acaaatgttc cactgaatcc tgtgaccctg tggcgtggtt cacctcctgt gttgtttgcc    6300
atgtgtgctc aggatgagct gattaaagct cttctcaggg gttcagtttt              6350
```

<210> SEQ ID NO 2
<211> LENGTH: 1340
<212> TYPE: DNA
<213> ORGANISM: mouse

<400> SEQUENCE: 2

```
gccttcccca gtcaggcaag aagcagcaag gtacaagaat acacagctcc aggctccaag      60
ggtcctgtgc gctcaggaag ttggtgcgga caatgttcat cttgcttgtg ttagtaactg     120
gagtttctgc tttcaccact ccaacagtgg tgcacacagg aaaggtttct gaatccccca    180
ttacatcgga gaagcccaca gtccatggag acaactgtca gtttcgtggc agagagttca    240
aatctgaatt gaggctggaa ggtgaacctg tggttctgag gtgccccttg gcacctcact    300
ccgacatctc cagcagttcc catagttttc tgacctggag taaattggac tcttctcagc    360
tgatcccaag agatgagcca aggatgtggg tgaagggtaa catactctgg attctgccag    420
cagtgcagca agactctggt acctacattt gcacattcag aaacgcatcc cactgtgagc    480
aaatgtctgt ggaactcaag gtctttaaga atactgaagc atctctgcct catgtctcct    540
acttgcaaat ctcagctctc tccaccaccg ggttactagt gtgccctgac ctgaaagaat    600
tcatctccag caacgctgat ggaaagatac agtggtataa gggcgccata ctcttggata    660
aaggcaataa ggaatttctg agtgcaggag accccacacg cctattgata tccaacacgt    720
ccatggacga tgcaggctat tacagatgtg ttatgacatt tacctacaat ggccaggaat    780
acaacatcac taggaatatt gaactccggg tcaaaggaac aaccacggaa cccatccctg    840
tgatcatttc tcccctggag acaataccag catcattggg gtcaagactg atagtcccgt    900
gcaaagtgtt tctgggaact ggtacatctt ccaacaccat tgtgtggtgg ttggctaaca    960
gcacgtttat ctcggctgct tacccaagag gccgtgtgac cgaggggcta caccaccagt   1020
actcagagaa tgatgaaaac tatgtggaag tgtcgctgat ttttgatcca gtcacaaggg   1080
aggatctgca tacagatttt aaatgtgttg cctcgaatcc acggagttct cagtcactcc   1140
ataccacagt caaagaagtc tcttccacgt tctcctggag cattgcgctg gcacctctgt   1200
ctctgatcat cttggttgtg gggcaatat ggatgcgcag acggtgtaaa cgcagggctg    1260
```

```
-continued gaaagacata tggactgacc aagctacgga ctgacaacca ggacttccct tccagcccaa    1320
actaaataaa ggaaatgaaa                                                1340
```